US007285526B2

(12) United States Patent  
Maroun

(10) Patent No.: US 7,285,526 B2
(45) Date of Patent: Oct. 23, 2007

(54) INTERFERON ANTAGONISTS USEFUL FOR THE TREATMENT OF INTERFERON RELATED DISEASES

(75) Inventor: Leonard E. Maroun, Lawrence, MA (US)

(73) Assignee: Meiogen Biotechnology Corporation, Beverly, MA (US)

( * ) Notice: Subject to any disclaimer, the term of this patent is extended or adjusted under 35 U.S.C. 154(b) by 0 days.

(21) Appl. No.: 10/284,740

(22) Filed: Oct. 31, 2002

(65) Prior Publication Data

US 2003/0138404 A1 Jul. 24, 2003

Related U.S. Application Data

(63) Continuation-in-part of application No. 09/845,260, filed on Apr. 30, 2001, now abandoned, which is a continuation of application No. 09/067,398, filed on Apr. 28, 1998, now abandoned, which is a continuation of application No. 08/502,519, filed on Jul. 14, 1995, now Pat. No. 5,780,027.

(51) Int. Cl.
*A61K 38/16* (2006.01)

(52) U.S. Cl. ............................................. 514/2; 514/8
(58) Field of Classification Search ................ 530/300, 530/350; 424/184.1, 85.1, 198.1
See application file for complete search history.

(56) References Cited

U.S. PATENT DOCUMENTS

| 4,766,106 | A | * | 8/1988 | Katre et al. ..................... 514/12 |
| 4,824,432 | A | | 4/1989 | Skurkovich et al. ............ 604/4 |
| 4,948,738 | A | | 8/1990 | Banchereau et al. ......... 456/531 |
| 4,973,556 | A | | 11/1990 | Bove et al. ............. 435/240.27 |
| 5,297,562 | A | | 3/1994 | Potter .......................... 128/898 |
| 5,780,027 | A | | 7/1998 | Maroun .................... 424/130.1 |
| 5,888,511 | A | | 3/1999 | Skurkovich et al. |
| 6,093,405 | A | | 7/2000 | Zagury et al. ............ 424/198.1 |
| 2006/0099224 | A1 | * | 5/2006 | Kim ........................ 424/199.1 |

OTHER PUBLICATIONS

Colamonici et al., J. of Biol. Chem., Jul. 7, 1995, 270(27):15974-78.*
Smith et al., WO 92/07944, May 17, 1992.*
Stewart et al., EP 0601052, Oct. 16, 1996.*
Shin et al., PNAS 92:2820-2824, Mar. 1995.*
Biwas et al., J. of Exp. Med., Sep. 1, 1992, 176(3):739-50.*
Capobianchi et al., AIDS Res. & Human Retroviruses, 9(10):957-62, 1993.*
Yamada et al. Neurosci Lett. 1994; 7: 181: 61-64.*
Li et al. BMC Medical Genetics. 2006; 7: 24.*
Skurkovich et al. Ann NY Acad Sci. 2005; 1051: 684-700.*
Borg et al. Curr Opin Rhematol. 2007; 19: 61-66.*
O'Shea, J.J. et al., (2002), "Cytokines and Autoimmunity", *Nature Reviews Immunology*, 2:37-45.

Le Page, C. et al., (2000), "Interferon activation and innate immunity", *Reviews in Immunogenetics*, 2:374-386.
Blasko, I. et al., (1999), "TNFα plus IFNγ induce the production of Alzheimer β-amyloid peptides and decrease the secretion of APPs", *The FASEB Journal*, 13:63-68.
Gringeri, A. et al., (1999), "Active Anti-Interferon-α Immunization: A European-Israeli, Randomized, Double-Blind, Placebo-Controlled Clinical Trial in 242 HIV-1-Infected Patients (the EURIS Study)", *Journal of Acquired Immune Deficiency Syndrome and Human Retrovirology*, 20(4):358-370.
Akwa, Y. et al., (1998), "Transgenic Expression of IFN-α in the Central Nervous System of Mice Protects Against Lethal Neurotropic Viral Infection but Induces Inflammation and Neurodegeneration", *The Journal of Immunology*, 161:5016-5026.
Maroun, L.E. et al., (1998), "The Untoward Side Effects of Interferon Therapy Correlate Well with the Spectrum of Symptoms that Make Up the Down Syndrome", *Down Syndrome Research and Practice*, 5(3):143-147.
Wiseman, B.F. et al., (1997), "Interferon and trisomy 16 mouse fetal heart development and function", *Cytogenet Cell Genet*, 77(Suppl. 1):30(Abstract).
Gringeri, A. et al., (1996), "Absence of Clinical, Virological, and Immunological Signs of Progression in HIV-1-Infected Patients Receiving Active Anti-Interferon-α Immunization: A 30-Month Follow-Up Report", *Journal of Acquired Immune Deficiency Syndromes and Human Retrovirology*, 13(1):55-67.
Alcamí, A. et al., (1995), "Vaccinia, Cowpox, and Camelpox Viruses Encode Soluble Gamma Interferon Receptors with Novel Broad Species Specificity", *Journal of Virology*, 69(8):4633-4639.
Fall, L.S. et al., (1995), "Biological effect of active anti-IFNα immunization in HIV-infected patients", *Biomed & Pharmacother*, 49:422-428.
Gringeri, A. et al., (1995), "Anti-Alpha Interferon Immunization: Safety and Immunogenicity in Asymptomatic HIV Positive Patients at High Risk of Disease Progression", *Cellular and Molecular Biology*, 41(3):381-387.
Moosmayer, D. et al., (1995), "A Bivalent Immunoadhesin of the Human Interferon-γ Receptor Is an Effective Inhibitor of IFN-γ Activity", *Journal of Interferon and Cytokine Research*, 15:1111-1115.
Przemioslo, R.T. et al., (1995), "Histological changes in small bowel mucosa induced by gliadin sensitive T lymphocytes can be blocked by anti-interferon γ antibody", *Gut*, 36:874-879.

(Continued)

Primary Examiner—Elizabeth C. Kemmerer
(74) Attorney, Agent, or Firm—McDermott Will & Emery LLP

(57) ABSTRACT

The present invention relates to a process for ameliorating or preventing diseases that are caused, in part, by an increased level of, and/or an abnormal responsivity to, interferon. Alzheimer's disease, HIV infection, Down syndrome, transplant rejection, autoimmune disease, and infant encephalitis are examples of such diseases. Specifically, the invention provides a method for treating subjects suffering from, or at risk for, such diseases by the administration of a pharmacological preparation of interferon binding proteins of mammalian and/or viral origin that antagonize interferon's action. This invention comprises compositions of interferon binding proteins that can inhibit the activity of interferon gamma plus interferon alpha such compositions along with their method of production and modification being described herein.

10 Claims, 14 Drawing Sheets

OTHER PUBLICATIONS

Figure 1A:
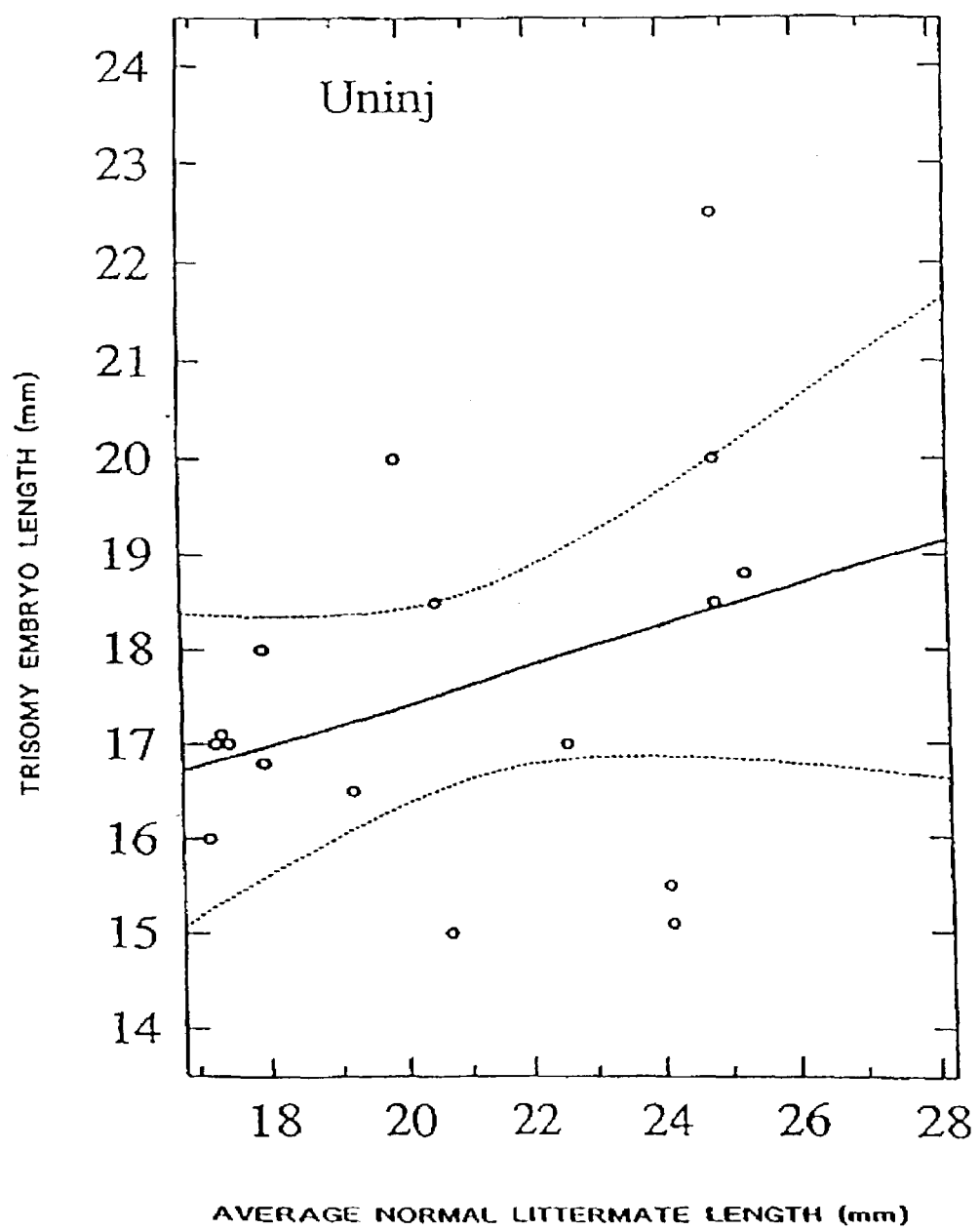

Symons, J.A. et al., (1995), "Vaccinia Virus Encodes a Soluble Type I Interferon Receptor of Novel Structure and Broad Species Specificity", *Cell*, 81:551-560.

Lachgar, A. et al., (1994), "Involvement of α-interferon in HIV-1 induced immunosuppression. A potential target for AIDS prophylaxis and treatment", *Biomed & Pharmacother*, 48:73-77.

Gringeri, A. et al., (1994), "A Randomized, Placebo-Controlled, Blind Anti-AIDS Clinical Trial: Safety and Immunogenicity of a Specific Anti-IFNα Immunization", *Journal of Acquired Immune Deficiency Syndromes*, 7(9):978-988.

Soh, J. et al., (1994), "Expression of a Functional Human Type I Interferon Receptor in Hamster Cells: Application of Functional Yeast Artificial Chromosome (YAC) Screening", *The Journal of Biological Chemistry*, 269(27):18102-18110.

Youngman, K.R. et al., (1994), "Inhibition of IFN-γ Activity in Supernatants from Stimulated Human Intestinal Mononuclear Cells Prevents Up-Regulation of the Polymeric Ig Receptor in an Intestinal Epithelial Cell Line", *J. Immunology*, 153:675-681.

Gerdes, A.M. et al., (1993), "Effect of increased gene dosage expression of the α-interferon receptors in Down's Syndrome", *Biochimica et Biophysica Acta*, 1181-135-140.

Haak-Frendscho, M. et al., (1993), "Inhibition of interferon-γ by an interferonγ receptor immunoadhesin", *Immunology*, 79:594-599.

Soh, J. et al., (1993), "Identification of a yeast artificial chromosome clone encoding an accessory factor for the human interferon γ receptor: Evidence for multiple accessory factors", *Proc. Natl. Acad. Sci. USA*, 90:8737-8741.

Holtzman, D.M. et al., (1992), "Dysregulation of gene expression in mouse trisomy 16, an animal model of Down Syndrome", *The EMBO Journal*, 11(2):619-627.

Sen, G.C. et al., (1992), "The Interferon System", *The Journal of Biological Chemistry*, 267(8):5017-5020.

Groner, Y. et al., (1990), "Down syndrome clinical symptoms are manifested in transfected cells and transgenic mice overexpressing the human Cu/Zn-superoxide dismutase gene", *J. Physiol. Paris*, 84:53-77.

Jung, V. et al., (1990), "Expression and Reconstitution of a Biologically Active Human Interferon-γ Receptor in Hamster Cells", *The Journal of Biological Chemistry*, 265(4):1827-1830.

Kato, K. et al., (1990), "Enhancement of S-100β Protein in Blood of Patients with Down's Syndrome", *J. Mol. Neurosci.*, 2:109-113.

Mann, D.M.A. et al., (1990), "The prevalence of amyloid (A4) protein deposits within the cerebral and cerebellar cortex in Down's syndrome and Alzheimer's disease", *Acta Neuropathol*, 80:318-327.

Bersu, E.T. et al., (1989), "Altered Placental Morphology Associated with Murine Trisomy 16 and Murine Trisomy 19", *Teratology*, 40:513-523.

Cronk, C. et al., (1988), "Growth Charts for Children with Down Syndrome: 1 Month to 18 Years of Age", *Pediatrics*, 81(1):102-110.

Plioplys, A.V., (1988), "Expression of the 210 kDa neurofilament subunit in culture central nervous system from normal and trisomy 16 mice: regulation by interferon", *Journal of the Neurological Sciences*, 85:209-222.

Gearhart, J.D. et al., (1986), "Autosomal Aneuploidy in Mice: Generation and Developmental Consequences", *Brain Research Bulletin*, 16:789-801.

Wisniewski, K.E. et al., (1986), "Neuronal Density and Synaptogenesis in the Postnatal Stage of Brain Maturation in Down Syndrome", *The Neurobiology of Down Syndrome*, 29-44.

Carr, J., (1985), "The Development of Intelligence", *Current Approaches to Down Syndrome*, Chapter 10:167-186.

Dussaix, E. et al., (1985), "Intrathecal synthesis of different alpha-interferons in patients with various neurological diseases", *Acta Neurol. Scand.*, 71:504-509.

Raziuddin, A. et al., (1984), "Receptors for human α and β interferon but not for γ interferon are specified by human chromosome 21", *Proc. Natl. Acad. Sci. USA*, 81:5504-5508.

Backman, K. et al., (1981)"Physical and genetic characterization of the *glnA-glnG* region of the *Escherichia coli* chromosome", *Proc. Natl. Acad. Sci. USA*, 78(6):3743-3747.

Maroun, L.E., (1980), "Interferon Action and Chromosome 21 Trisomy", *J. Theor. Biol.*, 86:603-606.

Gropp, A. et al., (1974), "Trisomy in the fetal backcross progeny of male and female metacentric heterozygotes of the mouse.I", *Cytogenet. Cell Genet.*, 13:511-535.

Tan, Y.H. et al., (1974), "Human Chromosome 21 Dosage: Effect on the Expression of the Interferon Induced Antiviral State", *Science*, 186:61-63.

Tan, Y.H. et al., (1973), "The Linkage of Genes for the Human Interferon-Induced Antiviral Protein and Indophenol Oxidase-B Traits to Chromosome G-21", *The Journal of Experimental Medicine*, 137:317-330.

Maroun, Leonard E. Anti-Interferon Immunoglobulins Can Improve the Trisomy 16 Mouse Phenotype. Teratology 51, 329-335 (1995).

Hallam, D.M. et al. Evidence for an interferon-related inflammatory reaction in the trisomy 16 mouse brain . . . J. of Neuroimm. 110, 66-75 (2000).

Shin, Seung-Uon et al. Transferrin-antibody fusion proteins are effective in brian targeting. Proc. Natl. Acad. Sci. USA 92, 2820-2824 (Mar. 1995).

Maroun, Leonard E. Anti-Interferon Immunoglobulins Can Improve the Trisomy 16 Mouse Phenotype. Teratology 51, 329-335 (1995).

* cited by examiner 1  2

GenBank Acc. No. M11026
(SEQ ID NO: 10)
```
MALSFSLLMA VLVLSYKSIC SLGCDLPQTH SLGNRRALIL LAQMGRISPF SCLKDRHDFG  60
LPQEEFDGNQ FQKTQAISVL HEMIQQTFNL FSTEDSSAAW EQSLLEKFST ELYQQLNNLE 120
ACVIQEVGME ETPLMNEDSI LAVRKYFQRI TLYLTEKKYS PCAWEVVRAE IMRSLSFSTN 180
LQKILRRKD                                                        189
```
(SEQ ID NO: 9)
```
gttcaaggtt acccatctca agtagcctag caacatttgc aacatcccaa tggccctgtc  60
cttttcttta ctgatggccg tgctggtgct cagctacaaa tccatctgtt ctctaggctg 120
tgatctgcct cagacccaca gcctgggtaa taggagggcc ttgatactcc tggcacaaat 180
gggaagaatc tctcctttct cctgcctgaa ggacagacat gactttggac ttccccagga 240
ggagtttgat ggcaaccagt tccagaagac tcaagccatc tctgtcctcc atgagatgat 300
ccagcagacc ttcaatctct tcagcacaga ggactcatct gctgcttggg aacagagcct 360
cctagaaaaa ttttccactg aactttacca gcaactgaat aacctggaag catgtgtgat 420
acaggaggtt gggatggaag agactcccct gatgaatgag gactccatcc tggctgtgag 480
gaaatacttc caaagaatca ctctttatct aacagagaag aaatacagcc cttgtgcctg 540
ggaggttgtc agagcagaaa tcatgagatc cctctctttt tcaacaaact tgcaaaaaat 600
attaaggagg aaggattgaa aactggttca acatggcaat gatcctgatt gactaataca 660
ttatctcaca ctttcatgag ttcctcaatt tcaaagactc acttctataa ccaccacgag 720
ttgaatcaaa attttcaaat gttttcagca gtgtaaagaa gcgtcgtgta tacctgtgca 780
ggcactagta ctttacagat gaccatgctg atgtctctgt tcatctattt atttaaatat 840
ttatttaatt attttttaaga tttaaattat ttttttatgt aatatcatgt gtacctttac 900
attgtggtga atgtaacaat atatgttctt catatttagc caatatatta atttcctttt 960
tcattaaatt tttactatac                                            980
```

GenBank Acc. No. M25460
(SEQ ID NO: 12)
```
MTNKCLLQIA LLLCFSTTAL SMSYNLLGFL QRSSNCQCQK LLWQLNGRLE YCLKDRRNFD  60
IPEEIKQLQQ FQKEDAAVTI YEMLQNIFAI FRQDSSSTGW NETIVENLLA NVYHQRNHLK 120
TVLEEKLEKE DFTRGKRMSS LHLKRYYGRI LHYLKAKEDS HCAWTIVRVE ILRNFYVINR 180
LTGYLRN                                                          187
```
(SEQ ID NO: 11)
```
gagtctaact gcaacccttc gaagcctttg ctctggcaca acaggtagta ggcgacactg  60
gtcgtgttgt tgacatgacc aacaagtgtc tcctccaaat tgctctcctg ttgtgcttct 120
ccacgacagc tcttttccatg agctacaact tgcttggatt cctacaaaga agcagcaatt 180
gtcagtgtca aagctcctg tggcaattga atgggaggct gaatactgc ctcaaggaca 240
ggaggaactt tgacatccct gaggagatta gcagctgca gcagttccag aaggaggacg 300
ccgcagtgac catctatgag atgctccaga acatctttgc tattttcaga caagattcat 360
cgagcactgg ctggaatgag actattgttg agaacctcct ggctaatgtc tatcatcaga 420
gaaaccatct gaagacagtc tggaagaaa aactggagaa agaagatttc accaggggaa 480
aacgcatgag cagtctgcac ctgaaaagat attatgggag gattctgcat tacctgaagg 540
ccaaggagga cagtcactgt gcctggacca tagtcagagt ggaaatccta aggaactttt 600
acgtcattaa cagacttaca ggttacctcc gaaactgaag atctcctagc ctgtgcctct 660
gggacgggac aattgcttca gcattcttc aaccagcaga tgctgtttaa gtgactgatg 720
gcgaatgtac tgcatatgaa aggacactag aagatttga aattttatt aaattatgag 780
gtattttat ttatttaaat tttatttgg aaataaatt attttggtg caaaagtc      838
```

Fig. 7A

GenBank Acc. No. X13274 (SEQ ID NO: 8)
(SEQ ID NO: 14)

| | | | | | |
|---|---|---|---|---|---|
| MKYTSYILAF | QLCIVLGSLG | CYCQDPYVKE | AENLKKYFNA | GHSDVADNGT | LFLGILKNWK 60 |
| EESDRKIMQS | QIVSFYFKLF | KNFKDDQSIQ | KSVETIKEDM | NVKFFNSNKK | KRDDFEKLTN 120 |
| YSVTDLNVQR | KAIHELIQVM | AELSPAAKTG | KRKRSQMLFQ | GRRASQ | 166 |

(SEQ ID NO: 13)

```
tgaagatcag ctattagaag agaaagatca gttaagtcct ttggacctga tcagcttgat   60
acaagaacta ctgatttcaa cttcttggc  ttaattctct cggaaacgat gaaatataca  120
agttatatct tggcttttca gctctgcatc gttttgggtt ctcttggctg ttactgccag  180
gacccatatg taaaagaagc agaaaacctt aagaaatatt ttaatgcagg tcattcagat  240
gtagcggata tggaactct  tttcttaggc attttgaaga attggaaaga ggagagtgac  300
agaaaaataa tgcagagcca aattgtctcc ttttacttca aactttttaa aaactttaaa  360
gatgaccaga gcatccaaaa gagtgtggag accatcaagg aagacatgaa tgtcaagttt  420
ttcaatagca acaaaaagaa acgagatgac ttcgaaaagc tgactaatta ttcggtaact  480
gacttgaatg tccaacgcaa agcaatacat gaactcatcc aagtgatggc tgaactgtcg  540
ccagcagcta aaacagggga gcgaaaaagg agtcagatgc tgtttcaagg tcgaagagca  600
tcccagtaat ggttgtcctg cctgcaatat ttgaatttta aatctaaatc tatttattaa  660
tatttaacat tatttatatg gggaatatat ttttagactc atcaatcaaa taagtattta  720
taatagcaac ttttgtgtaa tgaaaatgaa tatctattaa tatatgtatt atttataatt  780
cctatatcct gtgactgtct cacttaatcc tttgttttct gactaattag gcaaggctat  840
gtgattacaa ggctttatct caggggccaa ctaggcagcc aacctaagca agatcccatg  900
ggttgtgtgt ttatttcact tgatgataca atgaacactt ataagtgaag tgatactatc  960
cagttactgc cggtttgaaa atatgcctgc aatctgagcc agtgctttaa tggcatgtca  980
gacagaactt gaatgtgtca ggtgaccctg atgaaaacat agcatctcag gagatttcat 1040
gcctggtgct tccaaatatt gttgacaact gtgactgtac ccaaatggaa agtaactcat 1100
ttgttaaaat tatcaatatc taatatatat gaataaagtg taagttcaca act         1153
```

GenBank Acc. No. XM_071048 (SEQ ID NO: 10)
(SEQ ID NO: 16)

| | | | | | |
|---|---|---|---|---|---|
| MIIKHFFGTV | LVLLASTTIF | SLDLKLIIFQ | QRQVNQESLK | LLNKLQTLSI | QQCLPHRKNF 60 |
| LLPQKSLSPQ | QYQKGHTLAI | LHEMLQQIFS | LFRANISLDG | WEENHTEKFL | IQLHQQLEYL 120 |
| EALMGLEAEK | LSGTLGSDNL | RLQVKMYFRR | IHDYLENQDY | STCAWAIVQV | EISRCLFFVF 180 |
| SLTEKLSKQG | RPLNDMKQEL | TTEFRSPREG | EVKCT | | 225 |

(SEQ ID NO: 15)

```
atgattatca agcacttctt tggaactgtg ttggtgctgc tggcctctac cactatcttc   60
tctctagatt tgaaactgat tatcttccag caaagacaag tgaatcaaga aagtttaaaa  120
ctcttgaata gttgcaaac  cttgtcaatt cagcagtgtc taccacacag gaaaaacttt  180
ctgcttcctc agaagtcttt gagtcctcag cagtaccaaa aaggacacac tctggccatt  240
ctccatgaga tgcttcagca gatcttcagc ctcttcaggg caaatatttc tctggatggt  300
tgggaggaaa accacacgga gaaattcctc attcaacttc atcaacagct agaataccta  360
gaagcactca tgggactgga agcagagaag ctaagtggta ctttgggtag tgataacctt  420
agattacaag ttaaaatgta cttccgaagg atccatgatt acctggaaaa ccaggactac  480
agcacctgtg cctgggccat tgtccaagta gaaatcagcc gatgtctgtt ctttgtgttc  540
agtctcacag aaaaactgag caaacaagga agaccttga  cgacatgaa  gcaagagctt  600
actacagagt ttagaagccc gagggaagga gaagttaaat gtacatag              648
```

Fig. 7B

GenBank Acc. No. NM_002177 (SEQ ID NO: 11)
(SEQ ID NO: 18)

MALLFPLLAA LVMTSYSPVG SLGCDLPQNH GLLSRNTLVL LHQMRRISPF LCLKDRRDFR
FPQEMVKGSQ LQKAHVMSVL HEMLQQIFSL FHTERSSAAW NMTLLDQLHT GLHQQLQHLE
TCLLQVVGEG ESAGAISSPA LTLRRYFQGI RVYLKEKKYS DCAWEVVRME IMKSLFLSTN
MQERLRSKDR DLGSS
(SEQ ID NO: 17)

```
gatctggtaa acctgaagca aatatagaaa cctatagggc ctgacttcct acataaagta   60
aggagggtaa aaatggaggc tagaataagg gttaaaattt tgcttctaga acagagaaaa  120
tgatttttt  catatatata tgaatatata ttatatatac acatatatac atatattcac  180
tatagtgtgt atacataaat atataatata tatattgtta gtgtagtgtg tgtctgatta  240
tttacatgca tatagtatat acacttatga ctttagtacc cagacgtttt tcatttgatt  300
aagcattcat ttgtattgac acagctgaag tttactggag tttagctgaa gtctaatgca  360
aaattaatag attgttgtca tcctcttaag gtcataggga aacacacaa  atgaaaacag  420
taaaagaaac tgaaagtaca gagaaatgtt cagaaaatga aaccatgtg  tttcctatta  480
aaagccatgc atacaagcaa tgtcttcaga aaacctaggg tccaaggtta agccatatcc  540
cagctcagta aagccaggag catcctcatt tcccaatggc cctcctgttc cctctactgg  600
cagccctagt gatgaccagc tatagccctg ttggatctct gggctgtgat ctgcctcaga  660
accatggcct acttagcagg aacaccttgg tgcttctgca ccaaatgagg agaatctccc  720
ctttcttgtg tctcaaggac agaagagact tcaggttccc ccaggagatg gtaaaaggga  780
gccagttgca gaaggcccat gtcatgtctg tcctccatga gatgctgcag cagatcttca  840
gcctcttcca cacagagcgc tcctctgctg cctggaacat gaccctccta gaccaactcc  900
acactggact tcatcagcaa ctgcaacacc tggagacctg cttgctgcag gtagtgggag  960
aaggagaatc tgctggggca attagcagcc ctgcactgac cttgaggagg tacttccagg  980
gaatccgtgt ctacctgaaa gagaagaaat acagcgactg tgcctgggaa gttgtcagaa 1040
tggaaatcat gaaatccttg ttcttatcaa caaacatgca agaaagactg agaagtaaag 1100
atagagacct gggctcatct tgaaatgatt ctcattgatt aatttgccat ataacacttg 1160
cacattgac  tctggtcaat tcaaaagact cttatttcgg cttaatcac  agaattgact 1220
gaattagttc tgcaaatact ttgtcggtat attaagccag tatatgttaa aaagacttag 1280
gttcaggggc atcagtccct aagatgttat ttattttac  tcatttattt attcttacat 1340
tttatcatat ttatactatt tatattctta tataacaaat gtttgccttt acattgtatt 1400
aagataacaa aacatgttca gctttccatt tggttaaata ttgtatttg  ttatttatta 1460
aattattttc aaac                                                   1474
```

Fig. 7C

Fig. 8A

Vaccinia virus interferon gamma receptor (B8R) gene (GenBank Acc. No. AF016273)

Amino acid sequence (SEQ ID NO: 20)

MRYIILAVLFINSIHAKITSYKFESVNFDSKIEWTGDGLYNISLKNYGIKTWQTMYTNVP
EGTYDISAFPKNDFVSFWVKFEQGDYKVEEYCTGPPTVTLTEYDDHPYATRGSKKIPIYK
RGDMCDIYLLYTANFTFGDSKEPVPYDIDDYDCTSTGCSIDFVTTEKVCVTAQGATEGF
LEKITPWSSKVCLTPKKSVYTCAIRSKEDVPNFKDKMARVIKRKFN

Nucleotide sequence (SEQ ID NO: 19)

attcaacgca gaggtcacac gtgtagaata tctaccaaat tatcatgcca ttatgataag taccottata ttcacaaata tgatggtgat
gagcgacaat attctattac tgcagaggga aaatgctata aaggaataaa atatgaaata agtatgatca acgatgatac
tctattgaga aaacatactc ttaaaattgg atctacttat atatttgatc gtcatggaca tagtaataca tattattcaa aatatgattt
ttaaaaattt aaaatatatt atcacttcag tgacagtagt caaataacaa acaacaccat gagatatatt ataattctcg cagttttgtt
cattaatagt atacacgcta aaataactag ttataagttt gaatccgtca attttgattc caaaattgaa tggactgggg atggtctata
caatatatcc cttaaaaatt atggcatcaa gacgtggcaa acaatgtata caaatgtacc agaaggaaca tacgacatat
ccgcatttcc aaagaatgat ttcgtatctt tctgggttaa atttgaacaa ggcgattata aagtggaaga gtattgtacg ggaccaccga
ctgtaacatt aactgaatac gacgaccatc cgtatgctac tagaggtagc aaaaagattc ctatttacaa acgcggtgac
atgtgtgata tctacttgtt gtatacggct aacttcacat tcggagattc taaagaacca gtaccatatg atatcgatga ctacgattgc
acgtctacag gttgcagcat agactttgtc acaacagaaa aagtgtgcgt gacagcacag ggagccacag aagggttttct
cgaaaaaatt actccatgga gttcgaaagt atgtctgaca cctaaaaaga gtgtatatac atgcgcaatt agatccaaag
aagatgttcc caatttcaag gacaaaatgg ccagagttat caagagaaaa tttaactaaa tttctcggta gcacatcaaa tgatgttacc
acttttctta gcatgcttaa cttgactaaa tattcataac taattttat taatgataca aaaacgaaat aaaactgcat attatacact
ggttaacgcc cttataggct ctaaccattt tcaagatgag gtccctgatt atagtccttc tgttcccctc tatcatctac tccatgtcta
ttagacgatg tgagaagact gaagaggaaa catggggatt gaaaataggg ttgtgtataa ttgccaaaga tttctatccc
gaaagaactg attgcagtgt tcatctccca actgcaagtg aag

Fig. 8B

Vaccinia B18R-α/β binding proteins (GenBank Acc. No. A19579)

Amino acid sequence (SEQ ID NO: 21)

MTMKMMVHIYFVSLLLLLFHSYAIDIENEITEFFNKMRDTLPAKDSKWLNPACMFGGT
MNDIAALGEPFSAKCPPIEDSLLSHRYKDYVVKWERLEKNRRRQVSNKRVKHGDLWIA
NYTSKFSNRRYLCTVTTKNGDCVQGIVRSHIRKPPSCIPKTYELGTHDKYGIDLYCGILY
AKHYNNITWYKDNKEINIDDIKYSQTGKELIIHNPELEDSGRYDCYVHYDDVRIKNDIVV
SRCKILTVIPSQDHRFKLILDPKINVTIGEPANITCTAVSTSLLIDDVLIEWENPSGWLIGFD
FDVYSVLTSRGGITEATLYFENVTEEYIGNTYKCR GHNYYFEKTLTTTVVLE

Nucleotide sequence (SEQ ID NO: 22)

gacaattaac gatctttata atatatcgta tccacctacc aaagtatagt tgtatttttc tcatgcgatg tgtgtaaaaa aactgatatt
atataaatat tttagtgccg tataataaag atgacgatga aaatgatggt acatatatat ttcgtatcat tattgttatt gctattccac
agttacgcca tagacatcga aaatgaaatc acagaattct tcaataaaat gagagatact ctaccagcta aagactctaa
atggttgaat ccagcatgta tgttcggagg cacaatgaat gatatagccg ctctaggaga gccattcagc gcaaagtgtc
ctcctattga agacagtctt ttatcgcaca gatataaaga ctatgtggtt aaatgggaaa ggctagaaaa aaatagacgg
cgacaggttt ctaataaacg tgttaaacat ggtgatttat ggatagccaa ctatacatct aaattcagta accgtaggta tttgtgcacc
gtaactacaa agaatggtga ctgtgttcag ggtatagtta gatctcatat tagaaaacct ccttcatgca ttccaaaaac atatgaacta
ggtactcatg ataagtatgg catagactta tactgtggaa ttctttacgc aaaacattat aataatataa cttggtataa agataataag
gaaattaata tcgacgacat taagtattca caaacgggaa aggaattaat tattcataat ccagagttag aagatagcgg
aagatacgac tgttacgttc attacgacga cgttagaatc aagaatgata tcgtagtatc aagatgtaaa atacttacgg ttataccgtc
acaagaccac aggtttaaac taatactaga tccaaaaatc aacgtaacga taggagaacc tgccaatata acatgcactg
ctgtgtcaac gtcattattg attgacgatg tactgattga atgggaaaat ccatccggat ggcttatagg attcgatttt gatgtatact
ctgttttaac tagtagaggc ggtattaccg aggcgacctt gtactttgaa aatgttactg aagaatatat aggtaataca tataaatgtc
gtggacacaa ctattatttt gaaaaaaccc ttacaactac agtagtattg gagtaaatat acaatgcatt tttatataca ttactgaata
attattatta ttatttatat cgtatttgtg ctataacgcg actatctagg tatttgtatc tcaccgatag agaacatata aat

SEQUENCE LISTING

<160> NUMBER OF SEQ ID NOS: 22

<210> SEQ ID NO 1
<211> LENGTH: 21
<212> TYPE: DNA
<213> ORGANISM: artificial sequence
<220> FEATURE:
<223> OTHER INFORMATION: primer

<400> SEQUENCE: 1
atggctctcc tctttctcct a                                         21

<210> SEQ ID NO 2
<211> LENGTH: 27
<212> TYPE: DNA
<213> ORGANISM: artificial sequence
<220> FEATURE:
<223> OTHER INFORMATION: primer

<400> SEQUENCE: 2
tctagaacct tttatactgc tattgaa                                   27

<210> SEQ ID NO 3
<211> LENGTH: 25
<212> TYPE: DNA
<213> ORGANISM: artificial sequence
<220> FEATURE:
<223> OTHER INFORMATION: primer

<400> SEQUENCE: 3

```
tctagatggt gtgcagtgtc ggagc                                            25
```

<210> SEQ ID NO 4
<211> LENGTH: 24
<212> TYPE: DNA
<213> ORGANISM: artificial sequence
<220> FEATURE:
<223> OTHER INFORMATION: primer

<400> SEQUENCE: 4

```
cgtacggaaa gtgcaggctt ccag                                             24
```

<210> SEQ ID NO 5
<211> LENGTH: 19
<212> TYPE: DNA
<213> ORGANISM: artificial sequence
<220> FEATURE:
<223> OTHER INFORMATION: primer

<400> SEQUENCE: 5

```
atgagatata ttataattc                                                   19
```

<210> SEQ ID NO 6
<211> LENGTH: 22
<212> TYPE: DNA
<213> ORGANISM: artificial sequence
<220> FEATURE:
<223> OTHER INFORMATION: primer

<400> SEQUENCE: 6

```
tcattagtta aattttctct tg                                               22
```

<210> SEQ ID NO 7
<211> LENGTH: 21
<212> TYPE: DNA
<213> ORGANISM: artificial sequence
<220> FEATURE:
<223> OTHER INFORMATION: primer

<400> SEQUENCE: 7

```
agttacgcca tagacatcga a                                                21
```

<210> SEQ ID NO 8
<211> LENGTH: 24
<212> TYPE: DNA
<213> ORGANISM: artificial sequence
<220> FEATURE:
<223> OTHER INFORMATION: primer

<400> SEQUENCE: 8

```
tcattactcc aatactactg tagt                                             24
```

<210> SEQ ID NO 9
<211> LENGTH: 980
<212> TYPE: DNA
<213> ORGANISM: Homo sapiens
<220> FEATURE:
<221> NAME/KEY: CDS
<222> LOCATION: (50)..(619)
<223> OTHER INFORMATION:

<400> SEQUENCE: 9

```
gttcaaggtt acccatctca agtagcctag caacatttgc aacatccca atg gcc ctg      58
                                                     Met Ala Leu
                                                      1 tcc ttt tct tta ctg atg gcc gtg ctg gtg ctc agc tac aaa tcc atc       106
```

```
                Ser Phe Ser Leu Leu Met Ala Val Leu Val Leu Ser Tyr Lys Ser Ile
                  5                  10                  15 tgt tct cta ggc tgt gat ctg cct cag acc cac agc ctg ggt aat agg       154
Cys Ser Leu Gly Cys Asp Leu Pro Gln Thr His Ser Leu Gly Asn Arg
 20                  25                  30                  35 agg gcc ttg ata ctc ctg gca caa atg gga aga atc tct cct ttc tcc       202
Arg Ala Leu Ile Leu Leu Ala Gln Met Gly Arg Ile Ser Pro Phe Ser
                 40                  45                  50 tgc ctg aag gac aga cat gac ttt gga ctt ccc cag gag gag ttt gat       250
Cys Leu Lys Asp Arg His Asp Phe Gly Leu Pro Gln Glu Glu Phe Asp
             55                  60                  65 ggc aac cag ttc cag aag act caa gcc atc tct gtc ctc cat gag atg       298
Gly Asn Gln Phe Gln Lys Thr Gln Ala Ile Ser Val Leu His Glu Met
         70                  75                  80 atc cag cag acc ttc aat ctc ttc agc aca gag gac tca tct gct gct       346
Ile Gln Gln Thr Phe Asn Leu Phe Ser Thr Glu Asp Ser Ser Ala Ala
     85                  90                  95 tgg gaa cag agc ctc cta gaa aaa ttt tcc act gaa ctt tac cag caa       394
Trp Glu Gln Ser Leu Leu Glu Lys Phe Ser Thr Glu Leu Tyr Gln Gln
100                 105                 110                 115 ctg aat aac ctg gaa gca tgt gtg ata cag gag gtt ggg atg gaa gag       442
Leu Asn Asn Leu Glu Ala Cys Val Ile Gln Glu Val Gly Met Glu Glu
                120                 125                 130 act ccc ctg atg aat gag gac tcc atc ctg gct gtg agg aaa tac ttc       490
Thr Pro Leu Met Asn Glu Asp Ser Ile Leu Ala Val Arg Lys Tyr Phe
            135                 140                 145 caa aga atc act ctt tat cta aca gag aag aaa tac agc cct tgt gcc       538
Gln Arg Ile Thr Leu Tyr Leu Thr Glu Lys Lys Tyr Ser Pro Cys Ala
        150                 155                 160 tgg gag gtt gtc aga gca gaa atc atg aga tcc ctc tct ttt tca aca       586
Trp Glu Val Val Arg Ala Glu Ile Met Arg Ser Leu Ser Phe Ser Thr
    165                 170                 175 aac ttg caa aaa ata tta agg agg aag gat tga aaactggttc aacatggcaa     639
Asn Leu Gln Lys Ile Leu Arg Arg Lys Asp
180                 185 tgatcctgat tgactaatac attatctcac actttcatga gttcctcaat ttcaaagact     699
cacttctata accaccacga gttgaatcaa aattttcaaa tgttttcagc agtgtaaaga     759
agcgtcgtgt atacctgtgc aggcactagt actttacaga tgaccatgct gatgtctctg     819
ttcatctatt tatttaaata tttatttaat tattttttaag atttaaatta tttttttatg    879
taatatcatg tgtacccttta cattgtggtg aatgtaacaa tatatgttct tcatatttag    939
ccaatatatt aatttccttt ttcattaaat ttttactata c                         980

<210> SEQ ID NO 10
<211> LENGTH: 189
<212> TYPE: PRT
<213> ORGANISM: Homo sapiens

<400> SEQUENCE: 10

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
                20                  25                  30

Gly Asn Arg Arg Ala Leu Ile Leu Leu Ala Gln Met Gly Arg Ile Ser
            35                  40                  45

Pro Phe Ser Cys Leu Lys Asp Arg His Asp Phe Gly Leu Pro Gln Glu
        50                  55                  60
```

```
Glu Phe Asp Gly Asn Gln Phe Gln Lys Thr Gln Ala Ile Ser Val Leu
 65                  70                  75                  80

His Glu Met Ile Gln Gln Thr Phe Asn Leu Phe Ser Thr Glu Asp Ser
                 85                  90                  95

Ser Ala Ala Trp Glu Gln Ser Leu Leu Glu Lys Phe Ser Thr Glu Leu
            100                 105                 110

Tyr Gln Gln Leu Asn Asn Leu Glu Ala Cys Val Ile Gln Glu Val Gly
            115                 120                 125

Met Glu Glu Thr Pro Leu Met Asn Glu Asp Ser Ile Leu Ala Val Arg
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Ile Leu Arg Arg Lys Asp
                180                 185

<210> SEQ ID NO 11
<211> LENGTH: 838
<212> TYPE: DNA
<213> ORGANISM: Homo sapiens
<220> FEATURE:
<221> NAME/KEY: CDS
<222> LOCATION: (75)..(638)
<223> OTHER INFORMATION:

<400> SEQUENCE: 11
gagtctaact gcaaccttcc gaagcctttg ctctggcaca acaggtagta ggcgacactg      60
gtcgtgttgt tgac atg acc aac aag tgt ctc ctc caa att gct ctc ctg      110
              Met Thr Asn Lys Cys Leu Leu Gln Ile Ala Leu Leu
                1               5                  10 ttg tgc ttc tcc acg aca gct ctt tcc atg agc tac aac ttg ctt gga     158
Leu Cys Phe Ser Thr Thr Ala Leu Ser Met Ser Tyr Asn Leu Leu Gly
         15                  20                  25 ttc cta caa aga agc agc aat tgt cag tgt cag aag ctc ctg tgg caa     206
Phe Leu Gln Arg Ser Ser Asn Cys Gln Cys Gln Lys Leu Leu Trp Gln
 30                  35                  40 ttg aat ggg agg ctt gaa tac tgc ctc aag gac agg agg aac ttt gac     254
Leu Asn Gly Arg Leu Glu Tyr Cys Leu Lys Asp Arg Arg Asn Phe Asp
 45                  50                  55                  60 atc cct gag gag att aag cag ctg cag cag ttc cag aag gag gac gcc     302
Ile Pro Glu Glu Ile Lys Gln Leu Gln Gln Phe Gln Lys Glu Asp Ala
                 65                  70                  75 gca gtg acc atc tat gag atg ctc cag aac atc ttt gct att ttc aga     350
Ala Val Thr Ile Tyr Glu Met Leu Gln Asn Ile Phe Ala Ile Phe Arg
             80                  85                  90 caa gat tca tcg agc act ggc tgg aat gag act att gtt gag aac ctc     398
Gln Asp Ser Ser Ser Thr Gly Trp Asn Glu Thr Ile Val Glu Asn Leu
         95                 100                 105 ctg gct aat gtc tat cat cag aga aac cat ctg aag aca gtc ctg gaa     446
Leu Ala Asn Val Tyr His Gln Arg Asn His Leu Lys Thr Val Leu Glu
    110                 115                 120 gaa aaa ctg gag aaa gaa gat ttc acc agg gga aaa cgc atg agc agt     494
Glu Lys Leu Glu Lys Glu Asp Phe Thr Arg Gly Lys Arg Met Ser Ser
125                 130                 135                 140 ctg cac ctg aaa aga tat tat ggg agg att ctg cat tac ctg aag gcc     542
Leu His Leu Lys Arg Tyr Tyr Gly Arg Ile Leu His Tyr Leu Lys Ala
                145                 150                 155 aag gag gac agt cac tgt gcc tgg acc ata gtc aga gtg gaa atc cta     590
```

```
                Lys Glu Asp Ser His Cys Ala Trp Thr Ile Val Arg Val Glu Ile Leu
                                160                 165                 170 agg aac ttt tac gtc att aac aga ctt aca ggt tac ctc cga aac tga              638
Arg Asn Phe Tyr Val Ile Asn Arg Leu Thr Gly Tyr Leu Arg Asn
        175                 180                 185 agatctccta gcctgtgcct ctgggacggg acaattgctt caagcattct tcaaccagca            698
gatgctgttt aagtgactga tggcgaatgt actgcatatg aaaggacact agaagatttt            758 gaaatttta ttaaattatg aggtattttt atttatttaa attttatttt ggaaaataaa             818
ttatttttgg tgcaaaagtc                                                         838

<210> SEQ ID NO 12
<211> LENGTH: 187
<212> TYPE: PRT
<213> ORGANISM: Homo sapiens

<400> SEQUENCE: 12

Met Thr Asn Lys Cys Leu Leu Gln Ile Ala Leu Leu Cys Phe Ser
 1               5                  10                  15

Thr Thr Ala Leu Ser Met Ser Tyr Asn Leu Leu Gly Phe Leu Gln Arg
            20                  25                  30

Ser Ser Asn Cys Gln Cys Gln Lys Leu Leu Trp Gln Leu Asn Gly Arg
        35                  40                  45

Leu Glu Tyr Cys Leu Lys Asp Arg Arg Asn Phe Asp Ile Pro Glu Glu
    50                  55                  60

Ile Lys Gln Leu Gln Gln Phe Gln Lys Glu Asp Ala Ala Val Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Arg Asn His Leu Lys Thr Val Leu Glu Glu Lys Leu Glu
        115                 120                 125

Lys Glu Asp Phe Thr Arg Gly Lys Arg Met Ser Ser Leu His Leu Lys
    130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
            180                 185

<210> SEQ ID NO 13
<211> LENGTH: 1193
<212> TYPE: DNA
<213> ORGANISM: Homo sapiens
<220> FEATURE:
<221> NAME/KEY: CDS
<222> LOCATION: (109)..(609)
<223> OTHER INFORMATION:

<400> SEQUENCE: 13
tgaagatcag ctattagaag agaaagatca gttaagtcct ttggacctga tcagcttgat             60
acaagaacta ctgatttcaa cttctttggc ttaattctct cggaaacg atg aaa tat            117
                                                    Met Lys Tyr
                                                     1 aca agt tat atc ttg gct ttt cag ctc tgc atc gtt ttg ggt tct ctt            165
Thr Ser Tyr Ile Leu Ala Phe Gln Leu Cys Ile Val Leu Gly Ser Leu
```

|  |  |  |  |  |  |  |  |  |  |  |  |  |  |  |  |
|---|---|---|---|---|---|---|---|---|---|---|---|---|---|---|---|
| | | 5 | | | | | 10 | | | | | 15 | | | |

```
ggc tgt tac tgc cag gac cca tat gta aaa gaa gca gaa aac ctt aag     213
Gly Cys Tyr Cys Gln Asp Pro Tyr Val Lys Glu Ala Glu Asn Leu Lys
 20              25                  30                  35 aaa tat ttt aat gca ggt cat tca gat gta gcg gat aat gga act ctt     261
Lys Tyr Phe Asn Ala Gly His Ser Asp Val Ala Asp Asn Gly Thr Leu
                 40                  45                  50 ttc tta ggc att ttg aag aat tgg aaa gag gag agt gac aga aaa ata     309
Phe Leu Gly Ile Leu Lys Asn Trp Lys Glu Glu Ser Asp Arg Lys Ile
             55                  60                  65 atg cag agc caa att gtc tcc ttt tac ttc aaa ctt ttt aaa aac ttt     357
Met Gln Ser Gln Ile Val Ser Phe Tyr Phe Lys Leu Phe Lys Asn Phe
         70                  75                  80 aaa gat gac cag agc atc caa aag agt gtg gag acc atc aag gaa gac     405
Lys Asp Asp Gln Ser Ile Gln Lys Ser Val Glu Thr Ile Lys Glu Asp
     85                  90                  95 atg aat gtc aag ttt ttc aat agc aac aaa aag aaa cga gat gac ttc     453
Met Asn Val Lys Phe Phe Asn Ser Asn Lys Lys Lys Arg Asp Asp Phe
100                 105                 110                 115 gaa aag ctg act aat tat tcg gta act gac ttg aat gtc caa cgc aaa     501
Glu Lys Leu Thr Asn Tyr Ser Val Thr Asp Leu Asn Val Gln Arg Lys
                120                 125                 130 gca ata cat gaa ctc atc caa gtg atg gct gaa ctg tcg cca gca gct     549
Ala Ile His Glu Leu Ile Gln Val Met Ala Glu Leu Ser Pro Ala Ala
            135                 140                 145 aaa aca ggg aag cga aaa agg agt cag atg ctg ttt caa ggt cga aga     597
Lys Thr Gly Lys Arg Lys Arg Ser Gln Met Leu Phe Gln Gly Arg Arg
        150                 155                 160 gca tcc cag taa tggttgtcct gcctgcaata tttgaatttt aaatctaaat         649
Ala Ser Gln
    165 ctatttatta atatttaaca ttatttatat ggggaatata ttttagact catcaatcaa     709 ataagtattt ataatagcaa cttttgtgta atgaaaatga atatctatta atatatgtat    769 tatttataat tcctatatcc tgtgactgtc tcacttaatc ctttgttttc tgactaatta    829 ggcaaggcta tgtgattaca aggctttatc tcaggggcca actaggcagc caacctaagc    889 aagatcccat gggttgtgtg tttatttcac ttgatgatac aatgaacact tataagtgaa    949 gtgatactat ccagttactg ccggtttgaa aatatgcctg caatctgagc cagtgcttta   1009 atggcatgtc agacagaact tgaatgtgtc aggtgaccct gatgaaaaca tagcatctca   1069 ggagatttca tgcctggtgc ttccaaatat tgttgacaac tgtgactgta cccaaatgga   1129 aagtaactca tttgttaaaa ttatcaatat ctaatatata tgaataaagt gtaagttcac   1189 aact                                                               1193
```

<210> SEQ ID NO 14
<211> LENGTH: 166
<212> TYPE: PRT
<213> ORGANISM: Homo sapiens

<400> SEQUENCE: 14

```
Met Lys Tyr Thr Ser Tyr Ile Leu Ala Phe Gln Leu Cys Ile Val Leu
 1               5                  10                  15

Gly Ser Leu Gly Cys Tyr Cys Gln Asp Pro Tyr Val Lys Glu Ala Glu
             20                  25                  30

Asn Leu Lys Lys Tyr Phe Asn Ala Gly His Ser Asp Val Ala Asp Asn
         35                  40                  45
```

```
Gly Thr Leu Phe Leu Gly Ile Leu Lys Asn Trp Lys Glu Glu Ser Asp
         50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
130                 135                 140

Pro Ala Ala Lys Thr Gly Lys Arg Lys Arg Ser Gln Met Leu Phe Gln
145                 150                 155                 160

Gly Arg Arg Ala Ser Gln
                165
```

<210> SEQ ID NO 15
<211> LENGTH: 648
<212> TYPE: DNA
<213> ORGANISM: Homo sapiens
<220> FEATURE:
<221> NAME/KEY: CDS
<222> LOCATION: (1)..(648)
<223> OTHER INFORMATION:

<400> SEQUENCE: 15

```
atg att atc aag cac ttc ttt gga act gtg ttg gtg ctg ctg gcc tct      48
Met Ile Ile Lys His Phe Phe Gly Thr Val Leu Val Leu Leu Ala Ser
 1               5                  10                  15 acc act atc ttc tct cta gat ttg aaa ctg att atc ttc cag caa aga      96
Thr Thr Ile Phe Ser Leu Asp Leu Lys Leu Ile Ile Phe Gln Gln Arg
             20                  25                  30 caa gtg aat caa gaa agt tta aaa ctc ttg aat aag ttg caa acc ttg     144
Gln Val Asn Gln Glu Ser Leu Lys Leu Leu Asn Lys Leu Gln Thr Leu
         35                  40                  45 tca att cag cag tgt cta cca cac agg aaa aac ttt ctg ctt cct cag     192
Ser Ile Gln Gln Cys Leu Pro His Arg Lys Asn Phe Leu Leu Pro Gln
     50                  55                  60 aag tct ttg agt cct cag cag tac caa aaa gga cac act ctg gcc att     240
Lys Ser Leu Ser Pro Gln Gln Tyr Gln Lys Gly His Thr Leu Ala Ile
 65                  70                  75                  80 ctc cat gag atg ctt cag cag atc ttc agc ctc ttc agg gca aat att     288
Leu His Glu Met Leu Gln Gln Ile Phe Ser Leu Phe Arg Ala Asn Ile
                 85                  90                  95 tct ctg gat ggt tgg gag gaa aac cac acg gag aaa ttc ctc att caa     336
Ser Leu Asp Gly Trp Glu Glu Asn His Thr Glu Lys Phe Leu Ile Gln
            100                 105                 110 ctt cat caa cag cta gaa tac cta gaa gca ctc atg gga ctg gaa gca     384
Leu His Gln Gln Leu Glu Tyr Leu Glu Ala Leu Met Gly Leu Glu Ala
        115                 120                 125 gag aag cta agt ggt act ttg ggt agt gat aac ctt aga tta caa gtt     432
Glu Lys Leu Ser Gly Thr Leu Gly Ser Asp Asn Leu Arg Leu Gln Val
130                 135                 140 aaa atg tac ttc cga agg atc cat gat tac ctg gaa aac cag gac tac     480
Lys Met Tyr Phe Arg Arg Ile His Asp Tyr Leu Glu Asn Gln Asp Tyr
145                 150                 155                 160 agc acc tgt gcc tgg gcc att gtc caa gta gaa atc agc cga tgt ctg     528
Ser Thr Cys Ala Trp Ala Ile Val Gln Val Glu Ile Ser Arg Cys Leu
                165                 170                 175
```

```
ttc ttt gtg ttc agt ctc aca gaa aaa ctg agc aaa caa gga aga ccc      576
Phe Phe Val Phe Ser Leu Thr Glu Lys Leu Ser Lys Gln Gly Arg Pro
        180                 185                 190 ttg aac gac atg aag caa gag ctt act aca gag ttt aga agc ccg agg      624
Leu Asn Asp Met Lys Gln Glu Leu Thr Thr Glu Phe Arg Ser Pro Arg
    195                 200                 205 gaa gga gaa gtt aaa tgt aca tag                                      648
Glu Gly Glu Val Lys Cys Thr
210                 215

<210> SEQ ID NO 16
<211> LENGTH: 215
<212> TYPE: PRT
<213> ORGANISM: Homo sapiens

<400> SEQUENCE: 16

Met Ile Ile Lys His Phe Phe Gly Thr Val Leu Val Leu Leu Ala Ser
1               5                   10                  15

Thr Thr Ile Phe Ser Leu Asp Leu Lys Leu Ile Ile Phe Gln Gln Arg
            20                  25                  30

Gln Val Asn Gln Glu Ser Leu Lys Leu Leu Asn Lys Leu Gln Thr Leu
        35                  40                  45

Ser Ile Gln Gln Cys Leu Pro His Arg Lys Asn Phe Leu Leu Pro Gln
    50                  55                  60

Lys Ser Leu Ser Pro Gln Gln Tyr Gln Lys Gly His Thr Leu Ala Ile
65                  70                  75                  80

Leu His Glu Met Leu Gln Gln Ile Phe Ser Leu Phe Arg Ala Asn Ile
                85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
        115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
            180                 185                 190

Leu Asn Asp Met Lys Gln Glu Leu Thr Thr Glu Phe Arg Ser Pro Arg
        195                 200                 205

Glu Gly Glu Val Lys Cys Thr
    210                 215

<210> SEQ ID NO 17
<211> LENGTH: 1514
<212> TYPE: DNA
<213> ORGANISM: Homo sapiens
<220> FEATURE:
<221> NAME/KEY: CDS
<222> LOCATION: (576)..(1163)
<223> OTHER INFORMATION:

<400> SEQUENCE: 17
gatctggtaa acctgaagca aatatagaaa cctatagggc ctgacttcct acataaagta    60
aggagggtaa aaatggaggc tagaataagg gttaaaattt tgcttctaga acagagaaaa   120
```

```
tgattttttt catatatata tgaatatata ttatatatac acatatatac atatattcac        180
tatagtgtgt atacataaat ataatatata tatattgtta gtgtagtgtg tgtctgatta        240
tttacatgca tatagtatat acacttatga ctttagtacc cagacgtttt tcatttgatt        300
aagcattcat ttgtattgac acagctgaag tttactggag tttagctgaa gtctaatgca        360
aaattaatag attgttgtca tcctcttaag gtcataggga gaacacacaa atgaaaacag        420
taaaagaaac tgaaagtaca gagaaatgtt cagaaaatga aaaccatgtg tttcctatta        480
aaagccatgc atacaagcaa tgtcttcaga aaacctaggg tccaaggtta agccatatcc        540
cagctcagta aagccaggag catcctcatt tccca atg gcc ctc ctg ttc cct          593
                                        Met Ala Leu Leu Phe Pro
                                          1               5 cta ctg gca gcc cta gtg atg acc agc tat agc cct gtt gga tct ctg         641
Leu Leu Ala Ala Leu Val Met Thr Ser Tyr Ser Pro Val Gly Ser Leu
           10                  15                  20 ggc tgt gat ctg cct cag aac cat ggc cta ctt agc agg aac acc ttg         689
Gly Cys Asp Leu Pro Gln Asn His Gly Leu Leu Ser Arg Asn Thr Leu
        25                  30                  35 gtg ctt ctg cac caa atg agg aga atc tcc cct ttc ttg tgt ctc aag         737
Val Leu Leu His Gln Met Arg Arg Ile Ser Pro Phe Leu Cys Leu Lys
    40                  45                  50 gac aga aga gac ttc agg ttc ccc cag gag atg gta aaa ggg agc cag         785
Asp Arg Arg Asp Phe Arg Phe Pro Gln Glu Met Val Lys Gly Ser Gln
55                  60                  65                  70 ttg cag aag gcc cat gtc atg tct gtc ctc cat gag atg ctg cag cag         833
Leu Gln Lys Ala His Val Met Ser Val Leu His Glu Met Leu Gln Gln
                75                  80                  85 atc ttc agc ctc ttc cac aca gag cgc tcc tct gct gcc tgg aac atg         881
Ile Phe Ser Leu Phe His Thr Glu Arg Ser Ser Ala Ala Trp Asn Met
            90                  95                 100 acc ctc cta gac caa ctc cac act gga ctt cat cag caa ctg caa cac         929
Thr Leu Leu Asp Gln Leu His Thr Gly Leu His Gln Gln Leu Gln His
       105                 110                 115 ctg gag acc tgc ttg ctg cag gta gtg gga gaa gga gaa tct gct ggg         977
Leu Glu Thr Cys Leu Leu Gln Val Val Gly Glu Gly Glu Ser Ala Gly
   120                 125                 130 gca att agc agc cct gca ctg acc ttg agg agg tac ttc cag gga atc        1025
Ala Ile Ser Ser Pro Ala Leu Thr Leu Arg Arg Tyr Phe Gln Gly Ile
135                 140                 145                 150 cgt gtc tac ctg aaa gag aag aaa tac agc gac tgt gcc tgg gaa gtt        1073
Arg Val Tyr Leu Lys Glu Lys Lys Tyr Ser Asp Cys Ala Trp Glu Val
                155                 160                 165 gtc aga atg gaa atc atg aaa tcc ttg ttc tta tca aca aac atg caa        1121
Val Arg Met Glu Ile Met Lys Ser Leu Phe Leu Ser Thr Asn Met Gln
            170                 175                 180 gaa aga ctg aga agt aaa gat aga gac ctg ggc tca tct tga              1163
Glu Arg Leu Arg Ser Lys Asp Arg Asp Leu Gly Ser Ser
       185                 190                 195 aatgattctc attgattaat ttgccatata acacttgcac atgtgactct ggtcaattca      1223
aaagactctt atttcggctt taatcacaga attgactgaa ttagttctgc aaatactttg      1283
tcggtatatt aagccagtat atgttaaaaa gacttaggtt caggggcatc agtccctaag      1343
atgttattta tttttactca tttatttatt cttacatttt atcatattta tactatttat      1403
attcttatat aacaaatgtt tgcctttaca ttgtattaag ataacaaaac atgttcagct      1463
ttccatttgg ttaaatattg tattttgtta tttattaaat tatttttcaaa c              1514
```

-continued

<210> SEQ ID NO 18
<211> LENGTH: 195
<212> TYPE: PRT
<213> ORGANISM: Homo sapiens

<400> SEQUENCE: 18

```
Met Ala Leu Leu Phe Pro Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Gly Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
            180                 185                 190

Gly Ser Ser
        195
```

<210> SEQ ID NO 19
<211> LENGTH: 1333
<212> TYPE: DNA
<213> ORGANISM: Vaccinia virus
<220> FEATURE:
<221> NAME/KEY: CDS
<222> LOCATION: (319)..(999)
<223> OTHER INFORMATION:

<400> SEQUENCE: 19

```
attcaacgca gaggtcacac gtgtagaata tctaccaaat tatcatgcca ttatgataag      60 taccccttata ttcacaaata tgatggtgat gagcgacaat attctattac tgcagaggga    120
aaatgctata aaggaataaa atatgaaata agtatgatca acgatgatac tctattgaga    180
aaacatactc ttaaaattgg atctacttat atatttgatc gtcatggaca tagtaataca    240
tattattcaa aatatgatttt ttaaaaatttt aaaatatatt atcacttcag tgacagtagt    300
caaataacaa acaacacc atg aga tat att ata att ctc gca gtt ttg ttc        351
                    Met Arg Tyr Ile Ile Ile Leu Ala Val Leu Phe
                    1               5                   10 att aat agt ata cac gct aaa ata act agt tat aag ttt gaa tcc gtc       399
Ile Asn Ser Ile His Ala Lys Ile Thr Ser Tyr Lys Phe Glu Ser Val
        15                  20                  25 aat ttt gat tcc aaa att gaa tgg act ggg gat ggt cta tac aat ata       447
Asn Phe Asp Ser Lys Ile Glu Trp Thr Gly Asp Gly Leu Tyr Asn Ile
    30                  35                  40
```

```
tcc ctt aaa aat tat ggc atc aag acg tgg caa aca atg tat aca aat      495
Ser Leu Lys Asn Tyr Gly Ile Lys Thr Trp Gln Thr Met Tyr Thr Asn
    45                  50                  55 gta cca gaa gga aca tac gac ata tcc gca ttt cca aag aat gat ttc      543
Val Pro Glu Gly Thr Tyr Asp Ile Ser Ala Phe Pro Lys Asn Asp Phe
 60                  65                  70                  75 gta tct ttc tgg gtt aaa ttt gaa caa ggc gat tat aaa gtg gaa gag      591
Val Ser Phe Trp Val Lys Phe Glu Gln Gly Asp Tyr Lys Val Glu Glu
                 80                  85                  90 tat tgt acg gga cca ccg act gta aca tta act gaa tac gac gac cat      639
Tyr Cys Thr Gly Pro Pro Thr Val Thr Leu Thr Glu Tyr Asp Asp His
             95                 100                 105 ccg tat gct act aga ggt agc aaa aag att cct att tac aaa cgc ggt      687
Pro Tyr Ala Thr Arg Gly Ser Lys Lys Ile Pro Ile Tyr Lys Arg Gly
        110                 115                 120 gac atg tgt gat atc tac ttg ttg tat acg gct aac ttc aca ttc gga      735
Asp Met Cys Asp Ile Tyr Leu Leu Tyr Thr Ala Asn Phe Thr Phe Gly
    125                 130                 135 gat tct aaa gaa cca gta cca tat gat atc gat gac tac gat tgc acg      783
Asp Ser Lys Glu Pro Val Pro Tyr Asp Ile Asp Asp Tyr Asp Cys Thr
140                 145                 150                 155 tct aca ggt tgc agc ata gac ttt gtc aca aca gaa aaa gtg tgc gtg      831
Ser Thr Gly Cys Ser Ile Asp Phe Val Thr Thr Glu Lys Val Cys Val
                160                 165                 170 aca gca cag gga gcc aca gaa ggg ttt ctc gaa aaa att act cca tgg      879
Thr Ala Gln Gly Ala Thr Glu Gly Phe Leu Glu Lys Ile Thr Pro Trp
            175                 180                 185 agt tcg aaa gta tgt ctg aca cct aaa aag agt gta tat aca tgc gca      927
Ser Ser Lys Val Cys Leu Thr Pro Lys Lys Ser Val Tyr Thr Cys Ala
        190                 195                 200 att aga tcc aaa gaa gat gtt ccc aat ttc aag gac aaa atg gcc aga      975
Ile Arg Ser Lys Glu Asp Val Pro Asn Phe Lys Asp Lys Met Ala Arg
    205                 210                 215 gtt atc aag aga aaa ttt aac taa atttctcggt agcacatcaa atgatgttac    1029
Val Ile Lys Arg Lys Phe Asn
220                 225 cactttctct agcatgctta acttgactaa atattcataa ctaattttta ttaatgatac   1089
aaaaacgaaa taaaactgca tattatacac tggttaacgc ccttataggc tctaaccatt   1149
ttcaagatga ggtccctgat tatagtcctt ctgttcccct ctatcatcta ctccatgtct   1209
attagacgat gtgagaagac tgaagaggaa acatggggat tgaaaatagg gttgtgtata   1269
attgccaaag atttctatcc cgaaagaact gattgcagtg ttcatctccc aactgcaagt   1329
gaag                                                                1333
```

<210> SEQ ID NO 20
<211> LENGTH: 226
<212> TYPE: PRT
<213> ORGANISM: Vaccinia virus

<400> SEQUENCE: 20

```
Met Arg Tyr Ile Ile Ile Leu Ala Val Leu Phe Ile Asn Ser Ile His
1               5                  10                  15

Ala Lys Ile Thr Ser Tyr Lys Phe Glu Ser Val Asn Phe Asp Ser Lys
            20                  25                  30

Ile Glu Trp Thr Gly Asp Gly Leu Tyr Asn Ile Ser Leu Lys Asn Tyr
        35                  40                  45

Gly Ile Lys Thr Trp Gln Thr Met Tyr Thr Asn Val

```
                50                   55                    60
Tyr Asp Ile Ser Ala Phe Pro Lys Asn Asp Phe Val Ser Phe Trp Val
 65                  70                   75                   80

Lys Phe Glu Gln Gly Asp Tyr Lys Val Glu Glu Tyr Cys Thr Gly Pro
                 85                   90                   95

Pro Thr Val Thr Leu Thr Glu Tyr Asp Asp His Pro Tyr Ala Thr Arg
                100                  105                  110

Gly Ser Lys Lys Ile Pro Ile Tyr Lys Arg Gly Asp Met Cys Asp Ile
                115                  120                  125

Tyr Leu Leu Tyr Thr Ala Asn Phe Thr Phe Gly Asp Ser Lys Glu Pro
130                  135                  140

Val Pro Tyr Asp Ile Asp Asp Tyr Asp Cys Thr Ser Thr Gly Cys Ser
145                  150                  155                  160

Ile Asp Phe Val Thr Thr Glu Lys Val Cys Val Thr Ala Gln Gly Ala
                165                  170                  175

Thr Glu Gly Phe Leu Glu Lys Ile Thr Pro Trp Ser Ser Lys Val Cys
                180                  185                  190

Leu Thr Pro Lys Lys Ser Val Tyr Thr Cys Ala Ile Arg Ser Lys Glu
                195                  200                  205

Asp Val Pro Asn Phe Lys Asp Lys Met Ala Arg Val Ile Lys Arg Lys
                210                  215                  220

Phe Asn
225

<210> SEQ ID NO 21
<211> LENGTH: 1293
<212> TYPE: DNA
<213> ORGANISM: Vaccinia virus
<220> FEATURE:
<221> NAME/KEY: CDS
<222> LOCATION: (121)..(1176)
<223> OTHER INFORMATION:

<400> SEQUENCE: 21
gacaattaac gatctttata atatatcgta tccacctacc aaagtatagt tgtattttc      60 tcatgcgatg tgtgtaaaaa aactgatatt atataaatat tttagtgccg tataataaag    120 atg acg atg aaa atg atg gta cat ata tat ttc gta tca tta ttg tta     168
Met Thr Met Lys Met Met Val His Ile Tyr Phe Val Ser Leu Leu Leu
 1               5                  10                  15 ttg cta ttc cac agt tac gcc ata gac atc gaa aat gaa atc aca gaa    216
Leu Leu Phe His Ser Tyr Ala Ile Asp Ile Glu Asn Glu Ile Thr Glu
             20                  25                  30 ttc ttc aat aaa atg aga gat act cta cca gct aaa gac tct aaa tgg    264
Phe Phe Asn Lys Met Arg Asp Thr Leu Pro Ala Lys Asp Ser Lys Trp
         35                  40                  45 ttg aat cca gca tgt atg ttc gga ggc aca atg aat gat ata gcc gct    312
Leu Asn Pro Ala Cys Met Phe Gly Gly Thr Met Asn Asp Ile Ala Ala
     50                  55                  60 cta gga gag cca ttc agc gca aag tgt cct cct att gaa gac agt ctt    360
Leu Gly Glu Pro Phe Ser Ala Lys Cys Pro Pro Ile Glu Asp Ser Leu
 65                  70                  75                  80 tta tcg cac aga tat aaa gac tat gtg gtt aaa tgg gaa agg cta gaa    408
Leu Ser His Arg Tyr Lys Asp Tyr Val Val Lys Trp Glu Arg Leu Glu
                 85                  90                  95 aaa aat aga cgg cga cag gtt tct aat aaa cgt gtt aaa cat ggt gat    456
Lys Asn Arg Arg Arg Gln Val Ser Asn Lys Arg Val Lys His Gly Asp
            100                 105                 110
```

-continued

| | |
|---|---|
| tta tgg ata gcc aac tat aca tct aaa ttc agt a

-continued

```
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140
Ser His Ile Arg Lys Pro Pro Ser Cys Ile Pro Lys Thr Tyr Glu Leu
145                 150                 155                 160
Gly Thr His Asp Lys Tyr Gly Ile Asp Leu Tyr Cys Gly Ile Leu Tyr
                165                 170                 175
Ala Lys His Tyr Asn Asn Ile Thr Trp Tyr Lys Asp Asn Lys Glu Ile
            180                 185                 190
Asn Ile Asp Asp Ile Lys Tyr Ser Gln Thr Gly Lys Glu Leu Ile Ile
        195                 200                 205
His Asn Pro Glu Leu Glu Asp Ser Gly Arg Tyr Asp Cys Tyr Val His
    210                 215                 220
Tyr Asp Asp Val Arg Ile Lys Asn Asp Ile Val Val Ser Arg Cys Lys
225                 230                 235                 240
Ile Leu Thr Val Ile Pro Ser Gln Asp His Arg Phe Lys Leu Ile Leu
                245                 250                 255
Asp Pro Lys Ile Asn Val Thr Ile Gly Glu Pro Ala Asn Ile Thr Cys
            260                 265                 270
Thr Ala Val Ser Thr Ser Leu Leu Ile Asp Asp Val Leu Ile Glu Trp
        275                 280                 285
Glu Asn Pro Ser Gly Trp Leu Ile Gly Phe Asp Phe Asp Val Tyr Ser
    290                 295                 300
Val Leu Thr Ser Arg Gly Gly Ile Thr Glu Ala Thr Leu Tyr Phe Glu
305                 310                 315                 320
Asn Val Thr Glu Glu Tyr Ile Gly Asn Thr Tyr Lys Cys Arg Gly His
                325                 330                 335
Asn Tyr Tyr Phe Glu Lys Thr Leu Thr Thr Thr Val Val Leu Glu
            340                 345                 350
```

INTERFERON ANTAGONISTS USEFUL FOR THE TREATMENT OF INTERFERON RELATED DISEASES

RELATED APPLICATIONS

This application is a continuation-in-part of U.S. application Ser. No. 09/845,260, filed Apr. 30, 2001, now abandoned which is a continuation of U.S. application Ser. No. 09/067,398, filed Apr. 28, 1998, now abandoned, which is a continuation of U.S. application Ser. No. 08/502,519, filed Jul. 14, 1995, now U.S. Pat. No. 5,780,027. The entire teachings of the above applications are incorporated herein by reference.

1. BACKGROUND

1.1 Field of the Invention

The present invention relates to a process for ameliorating or preventing diseases that are caused, in part, by an increased level of, and/or an abnormal responsivity to, interferon. Alzheimer's disease, HIV infection, Down syndrome, transplant rejection, autoimmune disease, and infant encephalitis are examples of such diseases. Specifically, the invention provides a method for treating subjects suffering from, or at risk for, such diseases by the administration of a pharmacological preparation of interferon binding proteins of mammalian and/or viral origin that antagonize interferon's action. This invention comprises compositions of interferon binding proteins that can inhibit the activity of interferon OGY AND IMMUNOLOGY OF DOWN SYNDROME (Alan R. Liss, 1987). The publications of these studies have been accompanied by speculative conjectures that the altered responsivity to interferon played a role in the pathogenesis of lesions of Down syndrome. See, Maroun, L. E., 1980, J. Theoret. Biol. 86:603-606.

2.3. Down Syndrome and Animal Models of It

An animal model of Down syndrome has been constructed by use of the knowledge that human chromosome-21 is syntenic to mouse chromosome-16, i.e., that many of the genes present on each are homologs of each other. Mice having specified trisomies can be bred by use of parental mice having "Robertsonian" chromosomes, i.e., chromosomes that are essentially the centromeric fusion of two different murine chromosomes. A variety of such Robertsonian chromosomes have been identified, including at least two involving chromosome-16 and a second different chromosome: Rb(16.17) and Rb(6.16). Mice homozygous for any Robertsonian or combination of independent Robertsonian chromosomes are euploid and fertile.

The intercross ($F_1$) between an Rb(16.17) and an Rb(6.16) mouse is also fully diploid at each genetic locus, although errors in meiosis may cause reduced fertility. Note that in such an $F_1$ both the maternal and paternal chromosome-16 are a part of a Robertsonian chromosome.

Because of meiotic errors the outcross between a mouse having both two different Robertsonian chromosome-16's and a non-Robertsonian mouse gives rise to a trisomy-16 conceptus in between 15% and 20% of cases. Gearhart, J. D. et al., 1986, Brain Res. Bull. 16:789-801; Gropp, A. et al., 1975, Cytogenet. Cell Genet. 14:42-62. The murine trisomy-16 fetuses develop to term but do not live beyond birth by more than a few hours.

Examination of the fetal trisomy-16 and the post-partum human trisomy-21 reveals a number of analogous or parallel lesions. For this reason, the murine trisomy-16 construct is considered to be an animal model of Down syndrome. Epstein, C. J., THE METABOLIC BASIS OF INHERITED DISEASE, 6TH ED. pp 291-326 (McGraw-Hill, New York, 1989); Epstein, C. J. et al., 1985, Ann. N. Y. Acad. Sci. 450:157-168. Because a murine trisomy-16 fetus is not viable post partum, the opportunity to study the neurological pathology of the model has been limited. However, it is clear that in both human trisomy-21 and murine trisomy-16 there is an overall reduction in fetal size and particularly in the development of the fetal brain. Epstein, C. J., THE CONSEQUENCES OF CHROMOSOME IMBALANCE: PRINCIPLES, MECHANISMS AND MODELS (Cambridge University Press, New York, 1986). Further insights into the effects of murine trisomy-16 have been obtained by the formation of Ts16← →2N chimeras (Gearhart, J. D. et al., 1986, Brain Res. Bulletin 16:815-24) and by transplantation of fetal-derived Ts16 tissue into a 2N host (Holtzman, D. M. et al., 1992, Proc. Natl. Acad. Sci. 89:138387; Holtzman, D. M. et al., DOWN SYNDROME AND ALZHEIMER DISEASE, pp 227-44 (Wiley-Liss, New York, 1992).

2.4. Alzheimer's Disease and Amyloid Precursor Protein

Alzheimer's disease is a progressive dementia which is characterized by the precipitation of a peptide, termed an A β peptide, of about 40 amino acids within the brain and within the walls of blood vessels in the brain. The A β peptide is derived from the processing of a larger cell surface protein called the β Amyloid Precursor Protein (β APP). Production of the A β peptide is not per se pathological. The functions of both the A β peptide or β APP are unknown.

Several lines of evidence indicate that the deposition of the A β peptide is not merely correlative but rather causative of Alzheimer's disease. The gene encoding β APP is located on chromosome-21 and, as noted above, subjects having Down syndrome develop Alzheimer's disease. More directly, kinship groups have been identified among the many causes of familial Alzheimer's disease in which the inheritance of the Disease is linked to the inheritance of a gene encoding a mutated β APP, moreover the mutation is within the A β peptide itself. Reviewed Selkoe, D. J., 1994, Ann. Rev. Neurosci. 17:489-517. Transgenic mice, having multiple copies of such a mutant β APP gene, operatively linked to a strong, neuronal and glial cell specific promoter, develop the anatomical lesions of Alzheimer's disease at about 6-9 months of age. Games, D. et al., 1995, Nature 373:523.

There is a relationship between Down syndrome and Alzheimer's disease. The gene encoding the β APP is found on chromosome-21. Patients with Down syndrome are at increased risk of developing Alzheimer's disease or Alzheimer's-like pathology, most often by about the fifth decade of life although cases of earlier development have been reported. Mann, D. M. A. et al., 1990, Acta Neuropathol. 80:318-27.

2.5. AIDS and Increased IFN Levels

After a latency period that can last for many years, HIV infected individuals "convert" to the immunosuppressed state referred to as "AIDS". Acquired Immunodeficiency Syndrome ("AIDS") is a complex of various pathologies that is proceeded by and associated with increased levels of IFN-γ and IFN-α in the blood (Rossel, S. et al., 1989, J. Infectious Diseases 159:815-821) and IFN-α in the CSF (Rho, M B. et al., 1995, Brain, Behavior, and Immunity 9:366-77). Immunization with human IFN-α to reduce IFN levels is associated with the prevention of conversion to AIDS and improved prognosis for AIDS patients (Gringeri, A. et al., 1996, J AIDS and Human Retrovirology 13:55-67) as taught by Zagury, et al. (U.S. Pat. No. 6,093,405). However, this immunization procedure has serious limitations as it is both irreversible and unreliable.

Interferons, like cytokines in the body generally, do not act in the absence of antagonism (Van Weyenbergh, J. et al., 1998, J. Immunol. 161:1568-1574.; Paludan, S. R., 1998, Scand. J. Immunol. 48:459-468.; Ghosh, A. K. et al., 2001, J. Biol. Chem. 276:11041-11048) and/or synergy (Kwon, S. et al., 2001, Nitric Oxide 5:534-546.; Moore, P. E. et al., 2001, J. Appl. Physiol. 91:1467-1474.; Zhang, Y. et al., 2001, J. Interferon Cytokine Res. 21:843-850) caused by other cytokines or other interferon types. Note that some other cytokine combinations have been found to not be synergistic (Czuprynski, C. J. et al., 1992, Antimicrob. Agents Chemother. 36:68-70). In addition, the action of one type of interferon frequently can be mimicked or replaced by the action of another type of interferon (Hughes, T. K. et al., 1987, J Interferon Res. 7:603-614). There is speculation that if you inhibit IFN-γ and IFN-α then disease can be treated (Lachgar, A. et al., 1994, Biomed Pharmacother. 48:73-77, U.S. Pat. No. 5,780,027), however conflicting data in the literature suggests that combined treatment may, in some instances, not be more effective than monotherapy (Lukina, G. V. et al., 1998, Ter. Arkh. 70:32-37).

Presented herein is evidence demonstrating that the pathological negative effects of one type of interferon (IFN-γ) are in the body aided and enhanced in its negative effects by another type of interferon (IFN-α). These data demonstrate that the reduction of interferon bioactivity to relieve a pathological condition can be measurably improved by reducing the activity of both interferon types simultaneously. See, e.g., FIG. 3, which show the results of single vs. double knockout of interferon receptor genes.

3. SUMMARY OF THE INVENTION

The present invention is based, in part, on the recognition that in certain pathologic processes, the host is rendered hyperproductive and/or aberrantly sensitive to the effects of interferon so that the effects of interferon become an immediate and direct cause of the pathology. Such processes include, in humans, trisomy of chromosome-21 or the portion of the chromosome-21 that encodes the receptor for type I interferon and at least one component of the receptor for IFN-γ, which is the genetic abnormality associated with Down syndrome. Other diseases where IFN plays an important role include Alzheimer's disease and late-stage HIV infection.

The present invention provides a method of ameliorating the pathologic effects of interferon by administering to a subject, in the above-noted circumstances, an antagonist of interferon. Embodiments of the invention include the administration of antagonists, alone or in combination, that are antagonists of Type I interferon, Type II interferon (IFN-γ), and placental interferon (IFN-τ).

The present invention relates to compositions of interferon antagonists that inhibit the activity of interferons from either animal and/or human sources such compositions being comprised of proteins, or dimers or fragments thereof, that bind to IFN-γ together with proteins, or dimers or fragments thereof, that bind to IFN-α such compositions thus binding to and inhibiting both IFN-γ and IFN-α. The present invention encompasses pharmacologically useful formulations of proteins that bind to and inhibit interferon comprising at least one IFN-γ binding protein plus at least one protein that binds to and inhibits one or more IFN-α subtypes that are appropriately modified as needed to provide for increased serum half-life, reduced immunogenicity, efficient mode of administration, increased binding affinity, and/or enhanced blood brain barrier (BBB) penetration.

The invention features a composition for preventing or decreasing the pathological effects of a disease, where the pathological effects are associated with an increased level of or a heightened responsiveness to interferon, where the composition comprises at least two isolated interferon binding proteins, and where the composition inhibits the activity of at least two different species of interferon. The species of interferon can comprise IFN-α and IFN-γ. The isolated interferon binding proteins can include a first interferon binding protein that binds to IFN-α and a second interferon binding protein that binds to IFN-γ. One or more of the interferon binding proteins can be an IFN-α binding protein. One or more of the interferon binding proteins can be an IFN-γ binding protein. One of the interferon binding proteins can be the human IFN-γ receptor. The interferon binding proteins can be the B8R and B18R proteins of Vaccinia virus. One of the interferon binding proteins can be Vaccinia B18R IFN-α binding protein. One of the interferon binding proteins can be the Vaccinia B8R interferon-γ binding protein. One or more of the interferon binding proteins can be an antibody, or an antibody fragment. One or more of the interferon binding proteins can be an interferon-specific antibody. One or more of the interferon binding proteins can be an interferon-specific humanized antibody. Antibodies or antibody fragments can be PEGylated or fused with transferrin. The interferon binding proteins can be PEGylated or fused with transferrin.

In another aspect, the invention features a plurality of interferon binding proteins comprising two or more interferon binding proteins, where the interferon binding proteins bind to and inhibit the activity of one or more interferons (i.e., interferon species).

Any of the compositions can be used in a method of treating a disease caused by elevated levels of two or more interferons, where the method includes the step of administering a therapeutically effective amount of the composition. The disease can be Alzheimer's disease, Down's syndrome, infant encephalitis, or an autoimmune disease. The disease can be HIV. Administration of the composition can be used to prevent the onset of AIDS.

In a further aspect, the invention features a method of treating a disease, where the method includes the step of administering a therapeutically effective amount of a pair of interferon antagonists to a patient having or at risk of having said disease, where the administration results in a reduction in the level of bioavailable interferon, such that the disease in the patient is treated. The disease can be Alzheimer's disease, Down's syndrome, infant encephalitis, or an autoimmune disease. The disease can be HIV. Administration of the composition can be used to prevent the onset of AIDS. Administration of the composition can be used to prevent or ameliorate AIDS-associated dementia. The interferon antagonists can be PEGylated or fused with transferrin.

In an additional aspect, the invention features a method of treating or preventing transplant rejection, where the method includes administering a therapeutically effective amount of one or more interferon antagonists to a patient, wherein the administration of the interferon antagonist reduces the level of bioavailable interferon in the patient such that the transplant rejection is treated or prevented. The interferon antagonists can be PEGylated or fused with transferrin.

The invention also features a method of treating or preventing AIDS in an HIV-infected patient, where the method includes administering a therapeutically effective amount of one or more interferon antagonists to the HIV infected patient, where the administration of the interferon antagonist reduces the level of bioavailable interferon in the patient such that AIDS in the HIV-infected patient is treated or prevented. The interferon antagonists can be PEGylated or fused with transferrin. The one or more interferon antagonists can be a homodimer of the human IFN-γ receptor ligand binding subunits, or a heterodimer of the AR1 and AR2 ligand binding subunits of the human IFN-α receptor.

In an additional aspect, the invention features a method of treating or preventing IFN related disease using the B18R gene product or its homologs of viral or other origin. The B18R gene product or its homolog can be PEGylated, or fused to transferrin.

In a further aspect, the invention features a method of treating or preventing IFN related disease using the B8R gene product or its homologs of viral or other origin. The B18R gene product or its homolog can be PEGylated, or fused to transferrin.

The invention also features a composition for preventing or decreasing the pathological effects of a disease, wherein the pathological effects are associated with an increased level of or a heightened responsiveness to interferon, wherein said composition comprises one or more isolated interferon binding protein, and wherein the composition inhibits the activity of one or more species of interferon. The interferon binding protein can be PEGylated or fused with transferrin. The interferon binding protein can be PEGylated or fused with transferrin. The interferon binding protein can be B18R or B8R.

As used herein, "interferon binding proteins" refers to a protein or protein fragment or peptide that binds to interferons with a Kd binding constant of at least $10^{-3}$, preferably $10^{-5}$, more preferably $10^{-7}$ and most preferably $10^{-9}$ or less and inhibit the biological activity of the targeted interferon. The binding constants of typical interferon binding proteins are shown in Table 2, below.

As used herein, the term "interferons" refers to the different types of interferons (IFN), (Diaz, M. O. et al 1994, J Interferon Res. 14:221-222; Allen, D et al, 1996, J Interferon Res. 16:181-184). These five are designated α interferon (formerly α1), ω interferon (formerly ω2), β interferon, γ interferon, and τ interferon. The sequences of the α, β and γ interferons are shown in FIG. 7.

Interferon-α and -β are so-called type I interferons. They are secreted by a wide variety of cell types and have a wide range of functions. They are best known for their antiviral properties. They mediate their effects through the same receptor, which is present of the surfaces of virtually all nucleated cell types. Interferon-gamma (immune or type II interferon) is distinct in several ways from both interferon-alpha and -beta. It mediates its effects through a separate receptor from the one used by the type I interferons. In addition to having antiviral properties, it is especially noteworthy as a potent modulator of the functions of a wide range of cell types. Many of these functions are critical to the immune and inflammatory responses.

As used herein, INF-α refers to interferon-α subspecies and dimers thereof. INF-β refers to interferon-β subspecies and dimers thereof.

As used herein, to "inhibit the activity" refers to a decrease in the activity or available amount of an interferon that is at least 10%, preferably 10-30%, more preferably 30-50% and most preferably 50-100% decreased in the presence of one or more interferon binding proteins as compared to the activity of an interferon in the absence of the interferon binding proteins.

As used herein, the term "fusion polypeptide" or "fusion protein" refers to a polypeptide that is comprised of two or more amino acid sequences, wherein the two or more amino acid sequences are physically linked by a peptide bond and wherein the two or more amino acid sequences are not found linked in nature.

As used herein, an "iron transport protein" is a transferrin preferably selected from the group comprising human transferrin, lactoferrin, ovotransferrin and/or serum transferrin.

As used herein, "Vaccinia B18R IFN-α binding protein" refers to a glycoprotein (60-65 kDa; see FIG. 8 that exists in a soluble and a membrane-bound form. The protein functions as a type-1 interferon (IFN) receptor with broad species specificity. The B18R protein has high affinity for human IFN-α and also binds rabbit, bovine, rat, pig, and mouse IFN-α. Since the protein exists as a soluble extracellular and a cell surface protein it has the potential to block both autocrine and paracrine functions of IFN. The B18R protein has been shown to inhibit the antiviral potency of IFN-α-1, IFN-α-2, IFN-α-8/1/8, and IFN-Ω on human cells.

As used herein, "Vaccinia B8R interferon γ binding protein" refers to a protein encoded by the B8R open reading frame of vaccinia virus (see FIG. 8). B8R possesses a hydrophobic amino-terminal signal sequence but lacks a discernible membrane anchor domain, suggesting that the proteins may be secreted.

As used herein, "modified to enhance drug delivery" refers to modifications of interferon antagonists so as to facilitate their delivery to a target tissue. In one embodiment the invention includes post-translational modification of interferon antagonists (for example PEGylation or glycation). In a further embodiment the interferon antagonist is fused to a fusion protein. In a preferred embodiment the fusion protein is an iron transport protein that promotes transport of the interferon antagonist across the blood brain barrier. In a further embodiment, the interferon antagonist is fused to a fusion protein that is capable of multimerization.

As used herein, a "therapeutically effective amount" means the total amount of each active component of the pharmaceutical composition or method that is sufficient to show a meaningful patient benefit, i.e., in the treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. Generally, a composition will be administered in a single dose in the range of 100 μg-10 mg/kg body weight, preferably in the range of 1 μg-100 μg/kg body weight. This dosage may be repeated daily, weekly, monthly, yearly, or as considered appropriate by the treating physician.

As used herein, "interferon antagonist" refers to a biomolecule that binds to an interferon as defined herein and blocks the biological activity of the interferon. In a preferred embodiment the interferon antagonist of the invention is an interferon binding protein. The effective amount of an interferon antagonist needed to bind and block interferon proteins in the blood can be determined by assaying the concentration of bioavailable interferon. An effective dose of interferon antagonist is a dose that is sufficient to reduce the level of bioavailable interferon by between at least three to five fold, more preferably by about ten fold and most preferably by about twenty five fold below the normal levels of interferon. The interferon antagonist can be a mixture of antagonists that are specific for the various different types of interferon. When one type of interferon predominates, the antagonist can be an antagonist for only the predominate type of interferon that is present.

As used herein, "transplant rejection" refers to the immune response that results from the transfer of a donor's cells, tissues or organs into a histoincompatible host.

As used herein, "treating a disease" refers to arresting or otherwise ameliorating the symptoms of a disease at least 10%, preferably 20-50% and more preferably 75-100%.

As used herein, the term "autoimmune disease" refers to a disorder wherein the immune system of a mammal mounts a humoral or cellular immune response to the mammal's own tissue or has intrinsic abnormalities in its tissues preventing proper cell survival without inflammation.

Examples of autoimmune diseases include, but are not limited to, diabetes, rheumatoid arthritis, multiple sclerosis, lupus erythematosis, myasthenia gravis, scieroderma, Crohn's disease, ulcerative colitis, Hashimoto's disease, Graves' disease, Sjögren's syndrome, polyendocrine failure, vitiligo, peripheral neuropathy, graft-versus-host disease, autoimmnune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barré syndrome, hemochromatosis, Henoch-Schönlein purpura, idiopathic IgA nephropathy, insulin-dependent diabetes mellitus (IDDM), juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, stiff-man syndrome and thyroiditis.

As used herein, "infant encephalitis" refers to inflammation of the brain most commonly caused by a viral infection of the brain that occurs in young children. The most important viruses causing sporadic cases of encephalitis in immunocompetent adults are herpes simplex virus type 1 (HSV-1), varicella-zoster virus (VZV), and, less commonly, enteroviruses. Epidemics of encephalitis are caused by arboviruses, which belong to several different viral taxonomic groups including Alphavirus of the family Togaviridae (e.g., Eastern equine encephalitis virus, Western equine encephalitis virus), Flavivirus of the family Flaviviridae (e.g., St. Louis encephalitis virus, Powassan virus), and Bunyavirus of the family Bunyaviridae (e.g., California encephalitis virus serogroup, LaCrosse virus).

As used herein, "bioavailable" refers to the portion of interferon that can be absorbed, transported, and/or utilized physiologically.

As used herein, the term "immunoglobulin" or "antibody" refers to a conventional antibody molecule, as well as fragments thereof which are also specifically reactive with one of the subject polypeptides. Antibodies can be fragmented using conventional techniques, e.g., protein digestion, gene truncation, and the fragments screened for utility in the same manner as described herein for whole antibodies. For example, F(ab)$_2$ fragments can be generated by treating antibody with pepsin. The resulting F(ab)$_2$ fragment can be treated to reduce disulfide bridges to produce Fab fragments. The antibodies and antibody fragments can be screened for enhanced binding affinity using phage display technology. The antibody of the present invention is further intended to include bispecific, single-chain, and chimeric and humanized molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and its hypervariable portion thereof (FAB, FAB$_2$, etc.) as well as the hybridoma cell producing the antibodies are a further aspect of the present invention which find a specific industrial application in the field of diagnostics and monitoring of specific diseases, preferably the ones hereafter described. In a preferred embodiment, the immunoglobulin is humanized.

"Humanized antibody", as used herein, refers to antibody molecules in which amino acids have been replaced in the non-antigen binding regions in order to more closely resemble a human antibody, while still retaining the original binding ability. Methods for making humanized antibodies are described in U.S. Pat. Nos. 6,054,297, 5,859,205, which are hereby incorporated be reference in their entirety.

As used herein, "in frame" refers to the reading frame used for the translation of a fusion polypeptide nucleotide sequence. In a fusion polypeptide X-Y, coding sequences for polypeptide Y are said to be 'in frame' with upstream coding sequences for the polypeptide X if the translation of the coding sequences X-Y results in a fusion polypeptide wherein polypeptide X is fused to polypeptide Y.

Figure 3:
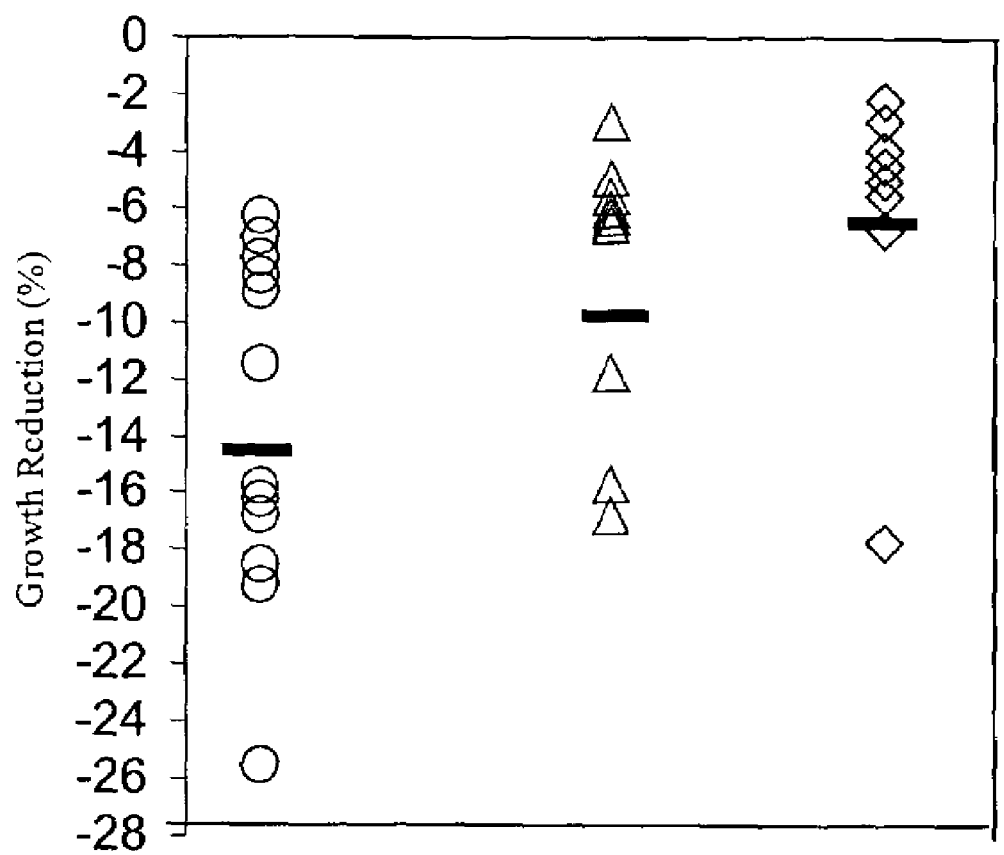

As used herein, the "pathological effects are associated with an increased level of, or a heightened responsiveness to, interferon" refers to a disease state that is associated with elevated levels of IFN receptors on the patient's cells or bioavailable interferon in the bodily fluids of a patient afflicted with the disease. For example, FIG. 3 shows evidence that the pathological negative effects of one type of interferon (IFN-γ), in this instance, growth retardation of a trisomy 16 mouse fetus, is enhanced in its negative effects by another type of interferon (IFN-α). These data on growth retardation also demonstrate that reduction of interferon bioactivity through gene knock out mutations in the IFN-γ and/or IFN-α/β receptors results in reduction in the pathological condition i.e., growth retardation and that this reduction is enhanced if the activity of both interferon types, i.e., IFN-γ and IFN-α are reduced simultaneously.

As used herein, the term "Human Immunodeficiency Virus" or "HIV" is meant to refer to all strains of human immunodeficiency viruses. Active human immunodeficiency virus infection results in a decline in the number of CD4$^+$ T cells, which in turn results in the incapacity of the infected individual to mount an effective immune response to viral, bacterial, fungal or parasitic infections.

As used herein, the "AIDS" refers to HIV infected patients with a CD4+ T cell count of less than <200/µL and who develop one of the HIV-associated diseases considered to be indicative of a severe defect in cell-mediated immunity, typically opportunistic infections by organisms such as *P. carinii*, atypical mycobacteria, CMV, fungi, and other organisms that do not ordinarily cause disease in the absence of a compromised immune system.

As used herein, AIDS in an HIV infected patient is said to be "treated" or "prevented" if the CD4+ T cell count remain at or increases to a value that is 25%, 50%, 75%, 90%, 99% or preferably equal to the CD4+ T cell count of a patient that is not infected with HIV.

As used herein, the onset of AIDS in an HIV infected patient is said to be "prevented" if the patient's CD4+ T cell count decreases no more than 25%, preferably 10%, most preferably 0% from the CD4+ T cell count of a patient who is not infected with HIV.

4. DESCRIPTION OF THE FIGURES

Figure 1B:
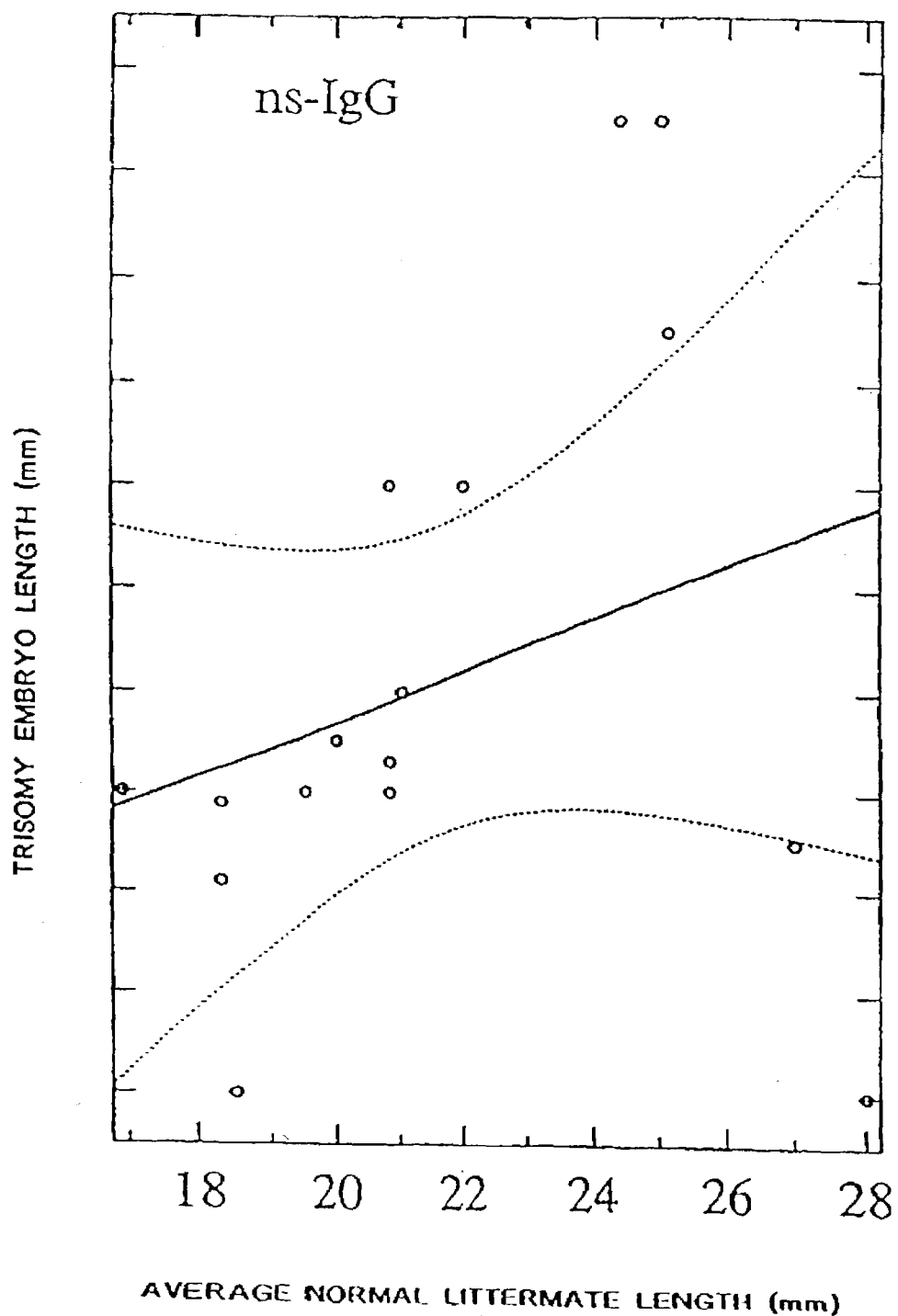
Figure 1C:
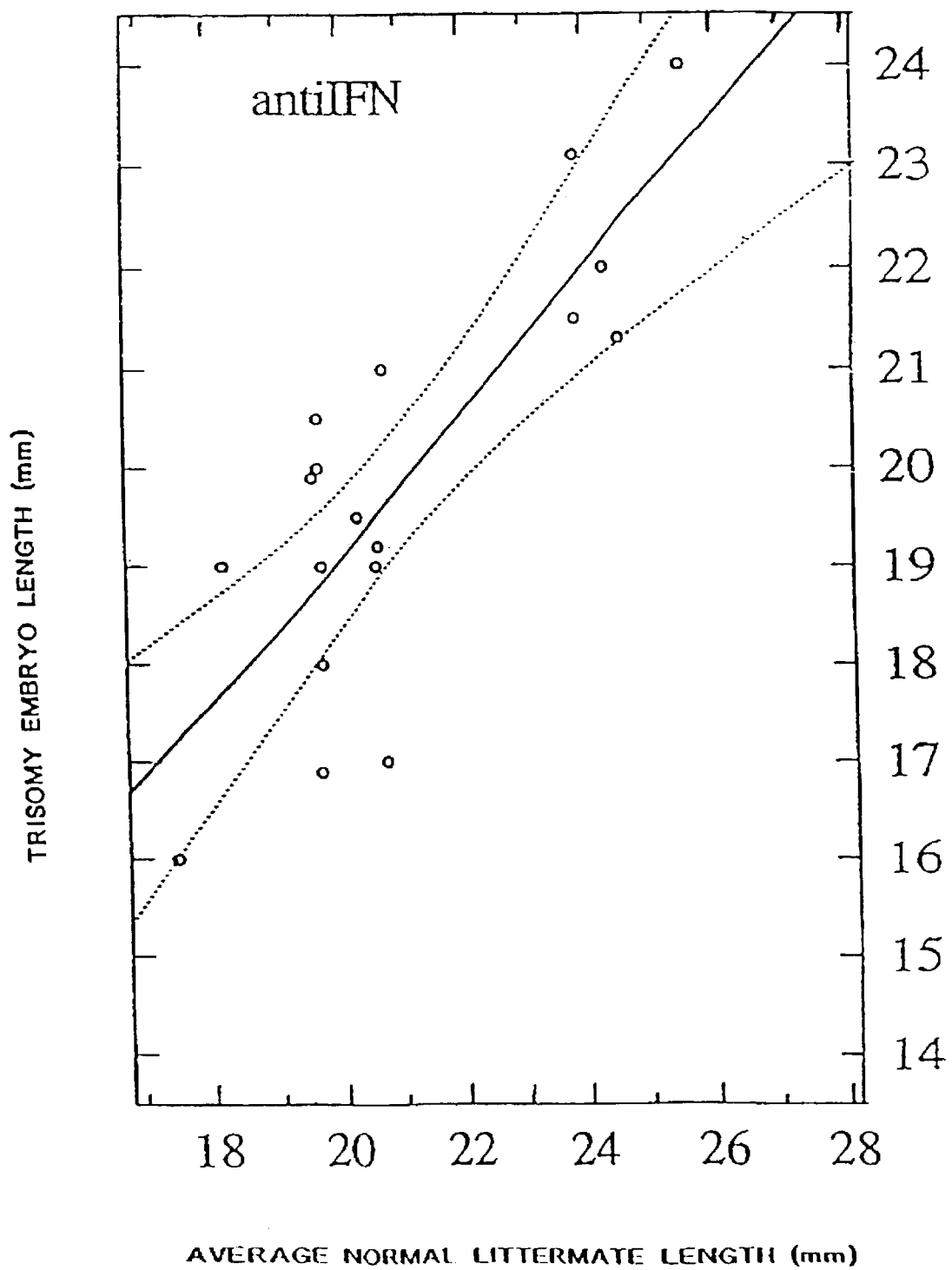

FIGS. 1A-1C. The lengths of Trisomy 16 fetuses plotted as a function of the average length of normal littermates. FIG. 1A, Uninjected controls; FIG. 1B, non-specific IgG (ns-IgG) injected controls; FIG. 1C, anti-IFN injected fetuses. An analysis-of-covariance was performed to compare the groups on length while adjusting for average normal littermate length. The lengths of the anti-IFN treated group were significantly greater than those of the ns-IgG injected controls (p=0.0112) and those of the uninjected controls (p=0.0037). The dotted lines in each figure encompass the 95% confidence limits.

Figure 2A:
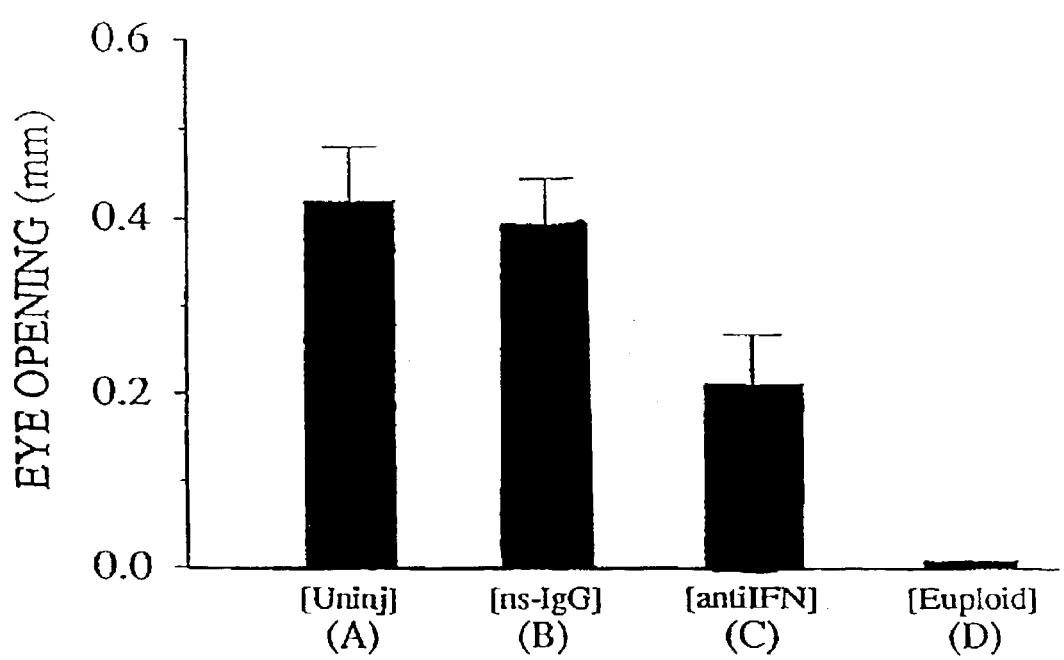
Figure 2B:
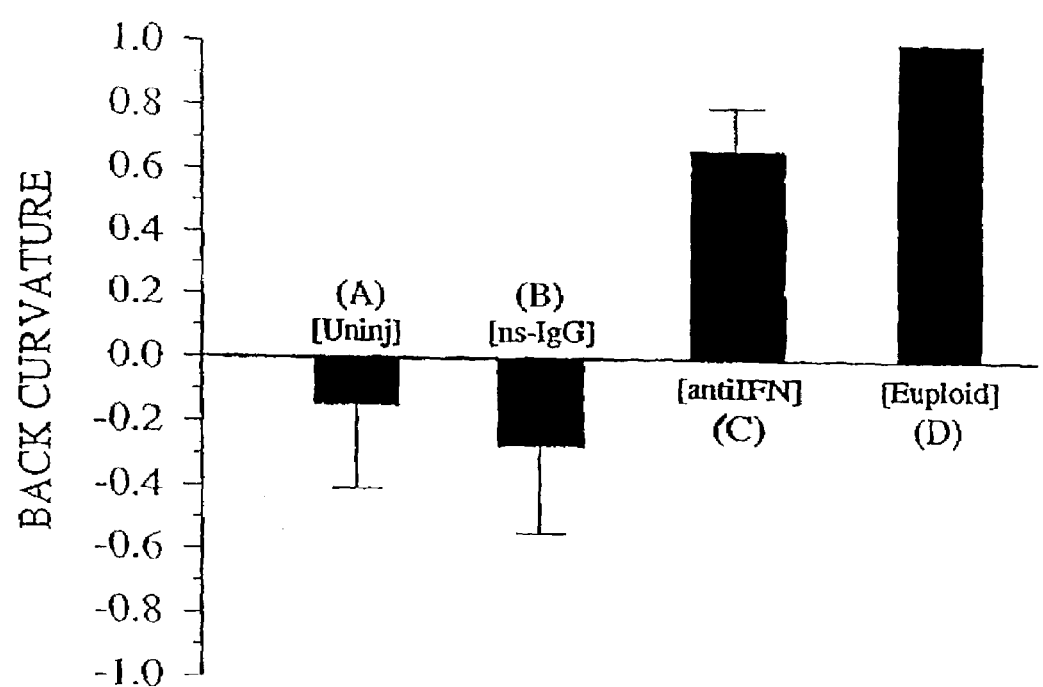

FIGS. 2A-2B. Morphometric analysis of the development in normal, Trisomy 16 treated and Trisomy 16 sham treated fetuses; FIG. 2A, average eye opening of 17 to 23 mm trisomy 16 fetuses; FIG. 2B, average back curvature scores of trisomy 16 fetuses greater than 20 mm in length. Columns: (A) Uninjected; (B) non-specific IgG injected; (C) anti-IFN injected; (D) euploid. The mean.+/−standard error is presented.

FIG. 3: Comparison of the improvement in trisomy 16 mouse fetus growth with a single (IFN-γ only) vs. double (IFN-γ plus IFN-α/β) receptor gene knockout. To produce the partial interferon receptor knockout trisomy (PIRKOT) mouse fetus, double IFN-γ+IFN-α/βR−/− knockout males (B & K International) were mated to double translocation females [Rb(6,16)24LuB×Rb(16,17)7BNRFI, Jackson Labs]. Crown-to-Rump length was measured on day 15-19 fetuses. Growth retardation is expressed as a percent of mean euploid littermate length. Knockout of a single IFN-γ receptor gene was sufficient to significantly improve trisomy fetus growth rate (mean growth retardation: 9.15+/−1.49%, N=9, p=0.043). However, the double knockout was measurably more effective (mean growth retardation: 6.81+/−1.6%, N=8, p=0.008).

Figure 4:
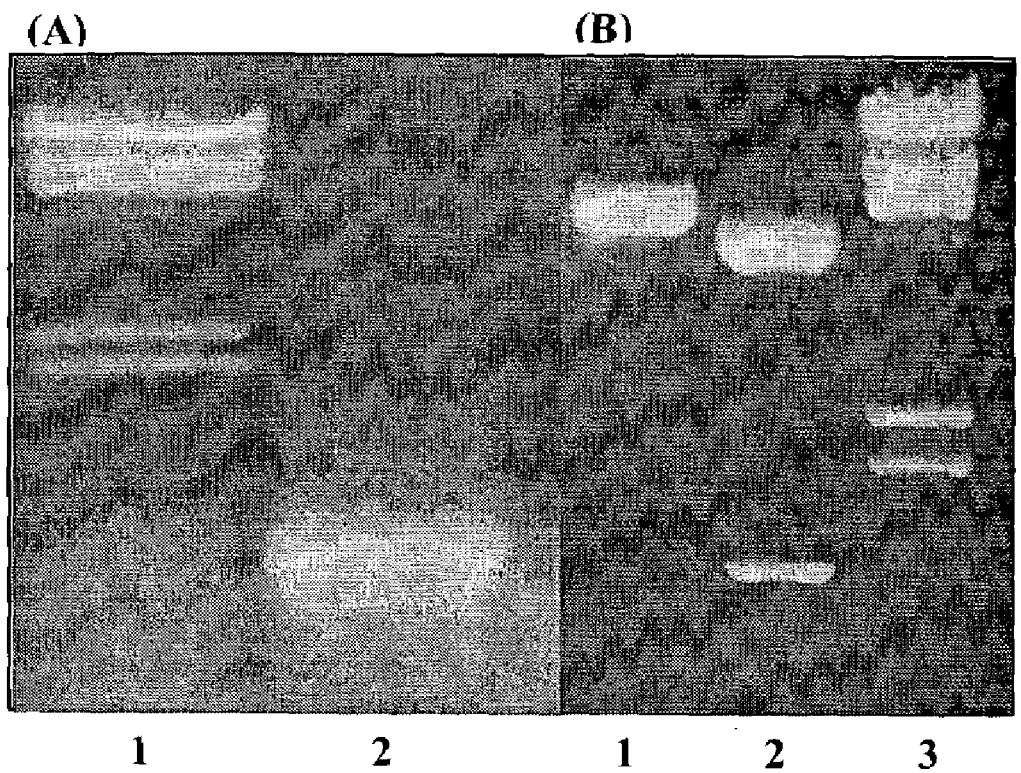

FIG. 4: Steps in the Cloning of Vaccinia IFN Inhibitor Genes. FIG. 4A: PCR amplification of the B18R Vaccinia gene (agarose gel electrophoresis). Lane 1: Lambda DNA HindIII digest markers; Lane 2: B18R gene PCR product (expected length, 999 bp). FIG. 4B: Restriction enzyme digests of the mammalian expression plasmid carrying the B18R Vaccinia gene (agarose gel electrophoresis). Lane 1: HindIII digest of the plasmid (there are no HindIII sites in the insert and there is one HindIII site in the original plasmid); Lane 2: BglII plasmid digest (there is one BglII site in the insert and one BglII site in the original plasmid); and Lane 3: Lambda DNA HindIII digest markers.

Figure 5:
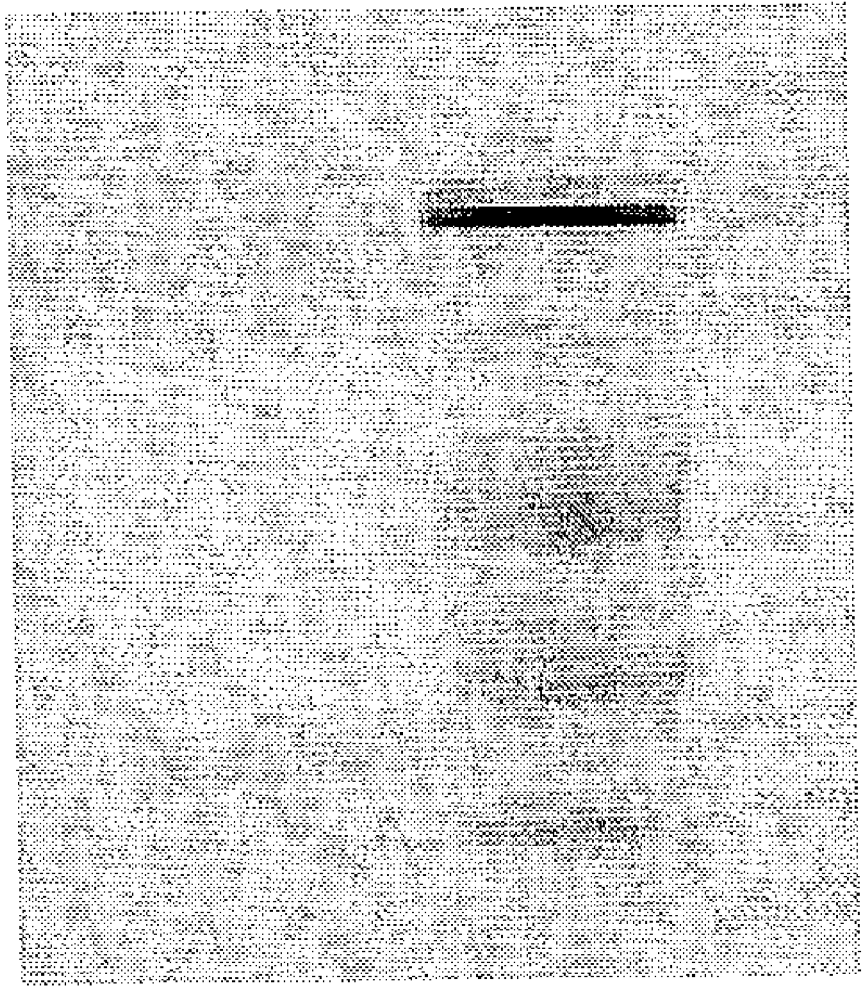

FIG. 5: Truncated human interferon γ receptor gene isolation. The human IFN-γ receptor gene is, by example, here isolated by PCR amplification from a thymus cDNA library (Clontech, Palo Alto, Calif. USA) for PCR subcloning into expression plasmids using the following primers: P1:ATGGCTCTCCTCTTTCTCCTA (SEQ ID NO: 1), P2:TCTAGAACCTTTTATACTGCTATTGAA (SEQ ID NO: 2). Lane 1: Truncated IFN-γ receptor gene. Lane 2: Lambda DNA markers.

Figure 6:
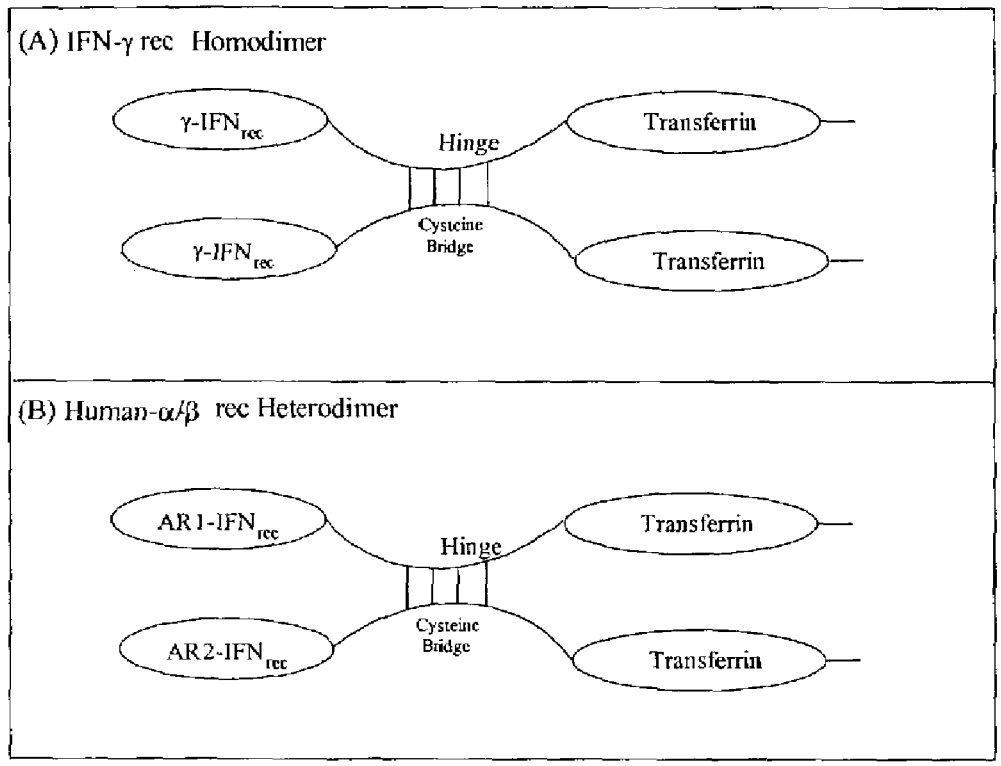

FIG. 6A: Example of a modified homodimer of the human IFN-γ receptor.

FIG. 6B: Example of a modified heterodimer with one copy each of both α-interferon receptor subunits (AR1 and AR2). The hinge region provides for two characteristics: (1) a flexible link to prevent receptor-Transferrin (Tf) mutual interference; and, (2) a signal to instruct the protein synthesis machinery of the eukaryotic cell to link two polypeptides together. The Tf provides the fusion protein with a longer serum half-life and the ability to be actively transported into the brain via the Tf receptors found lining the walls of the blood vessels of the brain.

FIG. 7: Genbank Accession numbers of the of the interferons.

FIGS. 8A and 8B: Nucleotide and amino acid sequence of B18R and B8R gene products of Vaccinia virus (B8R, GenBank Accession No.: AFO162273; B18R (FIG. 8A), GenBank Accession No.: D90076 (FIG. 8B)).

5. DETAILED DESCRIPTION OF THE INVENTION

The present invention provides a method of ameliorating the pathologic effects of interferon by administering to a subject, in the above-noted circumstances, an antagonist of interferon. Embodiments of the invention include the administration of antagonists, alone or in combination, that are antagonists of Type I interferon, Type II interferon (IFN-γ), and placental interferon (IFN-τ).

Many different species of virus produce interferon-binding proteins as a means of reducing the ability of the host to mount an immune response to infection. Examples of interferon binding proteins of the invention are depicted in Table 1, below, and share the property of being able to bind IFN-α or IFN-γ with high affinity, as shown in Table 2.

TABLE 1

|  | Gene Name (if applicable) | GenBank Acc. Nos. | Reference |
| --- | --- | --- | --- |
| IFN-gamma binding proteins Virus |  |  |  |
| Myxoma virus (strain Lausanne) | MT-7 | M81919 |  |
| Vaccinia virus (Modified virus Ankara strain) | B8R | AF016273 | J. Gen. Virol. 79:1159-1167 (1998) |
| Vaccinia virus (Praha strain) | B8R | AF120160 | Arch. Virol. 146:239-249 (2001) |
| Vaccinia virus (WR strain) | B8R | M58056 | Virology 180:633-647 (1991) |
| Vaccinia virus (strain not given) | B8R | D11079 |  |
| Vaccinia virus (strain Copenhagen) | B8R | M35027 | Virology 179:247-266 (1990) |
| Vaccinia virus (strain not given) | B8R | NC001559 | Virology 179:517-563 (1990) |
| Vaccinia virus (strain Ankara) | B18R | U94848 | unpublished |
| Vaccinia virus (strain Wyeth) | IFN g binding protein | AJ404659 | unpublished |
| Vaccinia virus (strain LIVP), isolates 2, 4 | IFN g binding protein | AJ404656, AJ404657 | unpublished |
| Vaccinia virus (strain Copenhagen) | IFN g binding protein | AJ404655 | unpublished |
| Ectromelia virus (strain Moscow) | IFN g binding protein | U19584 | Virology 208:762-769 (1995) |
| Rabbit fibroma virus | IFN-g receptor mimic; similar to vacB8R | AF170722, NC001266 |  |
| Rabbitpox virus (strain Utrecht) | IFN g binding protein | AJ404658 | unpublished |
| Camelpox virus (strain CMS) | soluble interferon-gamma receptor; similar to vaccinia B8R | AY009089 | J. Gen. Virol. 83:855-872 (2002) |

TABLE 1-continued

| | Gene Name (if applicable) | GenBank Acc. Nos. | Reference |
|---|---|---|---|
| Camelpox virus (isolate M-96 from Kazakhstan) | soluble interferon-gamma receptor; similar to vaccinia B8R | NC003391 | unpublished |
| Variola major virus (strain Bangladesh-1975) | homolog of vaccinia B8R (interferon-gamma receptor); putative | L22579 | Nature 366:748-751 (1993) |
| Variola virus (strain Somalia-1977) | B8R | U18341 | Virology 221:291-300 (1996) |
| Variola virus | B8R | NC001611, X69198 | FEBS Lett. 319:80-83 (1993) |
| Swinepox virus | similar to lumpy skin disease virus LSDV008 and vac B8R | NC003389 | J. Virol. 76:783-790 (2002) |
| Cowpox virus (strain GRI-90) | B8R | Y15035 | Virology 243:432-460 (1998) |
| Cowpox virus (strain Hamburg-1985) | IFN g binding protein | AJ404660 | unpublished |
| Cowpox virus (strain Turkmenia-1974) | IFN g binding protein | AJ404661 | unpublished |
| Monkeypox virus (strain Sierra Leone 70-0266) | IFN g binding protein | AJ404662 | unpublished |
| Monkeypox virus (strain Zaire 77-0666) | IFN g binding protein | AJ404663 | unpublished |
| IFN-alpha/beta binding proteins Virus | | | |
| Vaccinia virus (strain not given) | B18R | A19579 | none |
| Vaccinia virus (strain not given) | B18R | D11079 | |
| Vaccinia virus (strain Western reserve) | B18R | D01019, X56122 | Virology 177:588-594 (1990) |
| Vaccinia virus (strain Copenhagen) | B18R | M35027 | Virology 179:247-266 (1990) |
| Vaccinia virus (strain not given) | B18R | NC001559 | Virology 179:517-563 (1990) |
| Vaccinia virus (strain Ankara) | B18R | U94848 | unpublished |
| Vaccinia virus (strain Wyeth) | B18R | AJ269556 | J. Virol. 74:11230-11239 (2000) |
| Lumpy skin disease virus (isolate Neethling 2490) | LSDV135 putative IFN-alpha/beta binding protein | AE325528, NC003027 | J. Virol. 75:7122-7130 (2001) |
| Lumpy skin disease virus (strain Neethling) | interferon-binding protein | AH010683 | unpublished |
| Monkeypox virus (strain Zaire-96-I-16) | B18R | AF380138, NC003310 | FEBS Lett. 509:66-70 (2001) |
| Swinepox virus (isolate 17077-99) | SPV132 IFN-alpha/beta-like binding protein, similar to lumpy skin disease virus LSDV135 and vaccinia b18r | AF410153, NC003389 | J. Virol. 76:783-790 (2002) |
| Camelpox virus (isolate M-96 from Kazakhstan) | putative TFN-alpha/beta binding protein | AF438165, NC003391 | unpublished |
| Camelpox virus (strain CMS) | interferon-alpha/beta receptor; similar to vaccinia Bl9R | AY009089 | J. Gen. Virol. 83:855-872 (2002) |
| Cowpox virus (strain GRI-90) | B18R | Y15035 | Virology 243:432-460 (1998) |
| Variola major virus (strain Bangladesh-1975) | homolog of vaccinia virus CDS B18R; putative | L22579, P33795 | Nature 366:748-751 (1993) |
| Variola virus (strain Somalia-1977) | B18R | U18341 | Virology 221:291-300 (1996) |
| Ectromelia virus (strain Naval) | gene for interferon alpha/beta receptor | AJ319805 | J. Virol. 76:1124-1134 (2002) |
| Ectromelia virus (strain Hampstead) | gene for interferon alpha/beta receptor | AJ319804 | J. Virol. 76:1124-1134 (2002) |
| Ectromelia virus (strain Moscow) | gene for interferon alpha/beta receptor | AAC99571 | J. Virol. 76:1124-1134 (2002) |
| BeAn 58058 virus (isolate Brazil) | soluble IFN receptor gene homol to vac B18R | AF261890 | unpublished |

TABLE 2

Examples of binding constants of interferon binding proteins.

| | Kd | Reference |
|---|---|---|
| Gamma-IFN: | | |
| Myxoma M-T7 | $1.2 \times 10^{-9}$ M | Bai, H. et al., 2002, Biotechniques 32:160, 162-4, 166-71. |
| Vaccinia B8R | Undetermined | |
| Human gamma receptor | $1-2 \times 10^{-9}$ M | Fountoulakis, M. et al., 1990, J. Biol. Chem. 265:13268-75 |
| Alpha-IFN: | | |
| Vaccinia B18R | $174 \times 10^{-12}$ M | Symons, J. A. et al., 1995, Cell 81:551-60 |
| Human alpha receptor | $1 \times 10^{-7}$ M (in solution) $1 \times 10^{-9}$ M (cell surface) | Nguyen, N. Y. et al., 1996, J Interferon Cytokine Res 16 835-44 |

TABLE 2-continued

Examples of binding constants of interferon binding proteins.

| | Kd | Reference |
|---|---|---|
| Immunoglobin (Ig) | $10^{-11}$ M | Darsley, M. J. et al., 1985, Embo J. 4:383-92; Klein, B. et al., 1995, Immunol Today 16:216-20 |
| | $10^{-7}$ (Ag) to $10^{-8}$ M (peptide) | |

In order to ensure a successful infection, viruses use many different strategies to suppress or circumvent the host immune response. For example, the CrmA gene encoded by poxvirus functions by inhibiting interleukin-1 beta converting enzyme (Pickup, D. J., Infect. Agents Dis. 3(2-3):116-127 (1994), the SERP-1 gene of Myxoma virus encodes a serine protease inhibitor (McFadden, G. et al., J. Leukoc. Biol. 57(5):731-738 (1995)) and, the Myxoma virus encodes a TNF receptor homologue (T2, U.S. Pat. No. 5,464,938).

"Cytokine binding proteins" belong to a group of virally coded proteins termed "viroceptors" (Upton et al., Virology, 184:370 (1991)) as they act as decoy receptors to bind to cytokines thereby diverting the cytokine away from its normal host cell surface receptor. The term "virally encoded interferon binding proteins" refers to a viroceptor that binds to and inhibits one or more interferon types.

The Myxoma virus also encodes an IFN binding protein M-T7 that is described in U.S. Pat. No. 5,834,319. However, the M-T7 protein is of limited utility as it does not bind to interferon of human origin (see, e.g., U.S. Pat. No. 5,834,419). In contrast, the B8R and B18R proteins encoded by the poxviruses which are the subject of the present invention (FIG. 8) bind to and strongly inhibit the activity of human IFN-γ (B8R) and human IFN-α (B18R).

In some instances it may be preferable to use an IFN binding protein of human origin. The present invention describes highly modified forms of the human IFN-γ and IFN-α/β receptors that provide for increased binding affinity, serum half-life, and enhanced blood-brain-barrier (BBB) penetration.

5.1. Selection of Subjects

The present invention concerns the administration of interferon antagonists to subjects in order to ameliorate the neurological, pathological, and developmental abnormalities in the subject due to the action of interferon. A particular group of subjects at risk are subjects having a trisomy of the portion of the chromosome region, designated in humans 21q21.1-21.31, that encodes for interferon receptors. This group has the clinical diagnosis of Down syndrome. Grete, N., 1993, Eur. J. Hum. Genetics 1:51-63; Sinet, P. M., 1994, Biomed. & Pharmacol. 48:247-252. The homologous chromosome in mice is chromosome-16.

Diagnosis of Down syndrome can be made by any method known to the medical arts. Typically, for diagnosis in utero, amniocentesis can be performed at about 14 weeks of gestational age and chorionic villus sampling (biopsy) can be performed between 9 and 12 weeks of gestational age. Down syndrome in children and adults is diagnosed from karyotypes of peripheral blood cells. Cells from either type of sample are cultured and cytogenetic examination can be performed by methods well understood by those skilled in the art.

As noted above, patients having Down syndrome are at increased risk to develop Alzheimer's disease. A further group of subjects that would benefit from the invention consist of subjects having the diagnosis of probable Alzheimer's disease or who are at increased risk of developing Alzheimer's disease from causes other than Down syndrome. The diagnosis of probable Alzheimer's disease is made by clinical criteria (McKhann, G., 1984, Neurology 34:939; DIAGNOSTIC AND STATISTICAL MANUAL OF MENTAL DISORDERS IV, American Psychological Association, Washington, D.C.). Persons having a familial predisposition to Alzheimer's disease are also suitable subjects for the present invention.

HIV Infected Pre-AIDS and AIDS Patients

A further group of patients that would benefit from this invention consist of subjects having the diagnosis of HIV infection who have developed, or are at risk of developing, the AIDS complex of pathologies associated with immunosuppression. In these individuals, the conversion to the AIDS complex is proceeded by, and associated with, increased IFN-γ and IFN-α bioactivity which can be determined by various methods well known to the medical arts.

5.2. The Selection of Antagonists

The antagonist of the invention can be any antagonist that can be administered to the subject in an amount effective to prevent the deleterious action of the interferon.

The effective amount of antagonists that act by binding to and blocking interferon proteins in the blood can be determined by assaying the concentration of bioavailable interferon in the subjects blood. An effective dose of antagonist is a dose that is sufficient to reduce the level of bioavailable interferon by between at least three to five fold, more preferably by about ten fold and most preferably by about twenty five fold below the normal levels of interferon.

The assay of bioavailable interferon is performed by adding a sample of the subjects blood to a culture of an interferon sensitive cell line which is then infected with a test virus, typically Vesicular Stomatitis Virus (VSV), and the number of viral plaques is determined or the cytotoxic effects of the VSV infection is otherwise quantitated. Bioavailable interferon blocks productive viral infection. The level of bioavailable interferon is calculated by comparing various dilutions of the test sample with a titration of a standard sample of interferon. Such assays are routine in the art. See, e.g., Hahn, T. et al., 1980, in INTERFERON: PROPERTIES AND CLINICAL USES, ed. by A. Khan, N. O. Hill and G. L. Dorn, (Leland Fikes Foundation Press, Dallas, Tex.); Armstrong, J. A., 1971, Applied Microbiology 21:723-725; Havell, E. A. & Vilcek, J. 1972, Anti-microbial Agents and Chemotherapy 2:476-484.

In one embodiment of the invention the antagonist is a monoclonal anti-interferon antibody or fragment thereof. The production of such antibodies is well known in the art. The production of anti-IFN-α monoclonal antibodies that block interferon activity is taught by U.S. Pat. No. 4,973,556 to Bove et al. The production of blocking monoclonal antibodies to IFN-γ is taught by U.S. Pat. No. 4,948,738 to Banchereau. The structure of human trophoblastic interferon (IFN-τ) has been recently disclosed (Whaley, A. E., 1994, J. Biol. Chem. 269:10864-8). Monoclonal antibodies and other antagonists to this interferon can be produced using methods well known to those skilled in the art.

In a preferred embodiment, the antibody is a "chimeric" antibody, i.e., an antibody having a variable region from one species and a constant region from another species. Most typically chimeric antibodies for use in humans have constant regions of human origin. In an alternative preferred embodiment, the antibody is a "grafted" antibody, i.e., an antibody having complementarity determining regions from one species and a constant region and a framework region of the variable region from a second species. A grafted antibody in which the second species is human is termed a "humanized" antibody. Methods of making chimeric antibodies suitable for pharmaceutical use are disclosed in International Patent publication WO 92/16553 by Le, J. (Oct. 1, 1992). "Grafted" antibodies and "humanized" antibodies are described in U.S. Pat. No. 5,225,539 to Winter and International Patent publications WO 91/09967 and WO 92/11383 by Adair, J. R. et al. Suitable antagonists, smaller than an antibody molecule, can be derived from anti-interferon monoclonal antibodies by techniques well known in the art. See, e.g., U.S. Pat. No. 5,091,513 to Huston and U.S. Pat. No. 5,260,203 to Ladner. As used herein the term "antibody antagonists" includes natural polyclonal and monoclonal antibodies, chimeric and grafted antibodies, and antibodies produced by human antibody gene trangenic animals, and enzymatically and recombinantly produced interferon binding fragments of each type of antibody.

In an alternative embodiment the antagonist can be a recombinantly produced protein that comprises the interferon binding portion of an interferon receptor. The production of soluble interferon receptors by baculovirus transduced cells is described in Fountoulakis et al., 1991, Eur. J. Biochem. 198:441-450. Alternatively the antagonist can be a fusion protein that contains an interferon binding domain of an interferon receptor.

In alternative embodiments, the antagonist can be an antibody to an interferon receptor, a soluble interferon receptor, receptor fragment, or a peptide that is derived from an interferon that occupies the receptor binding site but does not activate the receptor. Such an IFN-γ peptide antagonist is disclosed by Jarpe, M. A. et al., 1993, J. Interferon Res. 13:99-103.

When the subject is a fetus, or an infant less than 6 weeks of age, the blood brain barrier is not fully formed. In these circumstances antibodies and other proteins that block the interferon receptor can directly reach the central nervous system. When the subject has an intact blood brain barrier, an embodiment of the invention can employ antibodies and proteins that block interferon by binding the interferon directly, rather than those that act at the interferon receptor.

Alternatively, increased CNS entry of antibody antagonists can be obtained by chemical modification of the antagonist. Such modifications include cationization, Pardridge, W., 1991, "Peptide Drug Delivery to the Brain", and glycation, Poduslo, J. F. & Curran, G. L., 1994, Molecular Brain Research 23:157.

The interferon antagonist can be a mixture of antagonists that are specific for the various different types of interferon. When one type of interferon predominates, the antagonist can be an antagonist for only the predominate type of interferon that is present.

When the subject is a fetus, then the antagonist can be administered by a transplacental route, e.g., antibody that is transported across the placenta. The human isotypes IgG1, IgG3 and IgG4 are suitable for transplacental administration.

5.2.1 Interferon Antagonists

In a preferred embodiment, Interferon binding proteins particularly useful for the formulation of the type of interferon antagonist described in the present invention are the B18R and B8R gene products of Vaccinia virus (B8R; B18R, see FIG. 8). The B8R protein is an IFN-γ binding protein that will bind and inhibit IFN-γ from human, rat, or rabbit sources (Alcami, A. et al., 1995, J. Virol. 69:4633-4639). The cross-species binding ability of these proteins greatly improves their utility as their ability to bind interferon, and the side effects of this binding, can be tested in animals prior to the start of human trials. In addition, the B18R protein is an IFN-α binding protein that is a single polypeptide that will bind and inhibit numerous subspecies of IFN-α from various sources (e.g., human, rat, mouse, or rabbit) (Symons, J. A. et al., 1995, Cell. 81:551-560).

In another embodiment, the invention is comprised of proteins of both viral and human origin. For example, the human IFN-γ receptor, or dimer or fragment or modification thereof, could be in a composition with the Vaccinia B18R protein, or dimer or fragment or modification thereof. The isolation and preparation of IFN-γ receptors is taught by U.S. Pat. Nos. 5,578,707, 5,221,789, and 5,763,210. The human IFN-γ ligand-binding gene can be cloned and expressed using standard procedures. For example, this gene can be PCR amplified from a thymus cDNA library (Clontech, Palo Alto, Calif., USA) using the procedures and primers described herein (see FIG. 5).

The genes encoding the IFN binding proteins of the invention can be isolated and expressed in prokaryotic or eukaryotic systems using methods familiar to those practiced in the art of gene cloning and expression.

5.2.2 Interferon Antagonist Fusion Proteins

The invention provides for interferon antagonist fusion proteins, fragments, dimers and modifications thereof. Methods used to link the cDNA nucleic acid encoding a gene of interest, or portion thereof, in frame, to a nucleic acid encoding interferon antagonist are well known to those in the art and are described extensively in Ausubel et al., eds., *Current Protocols in Molecular Biology*, John Wiley & Sons, Inc., 1995, with supplemental updates. The encoded-protein of interest may be linked in-frame to the amino-or carboxyl-terminus of the interferon antagonist. The nucleic acid encoding the chimeric protein is then linked in operable association to a promoter element of a suitable expression vector. Fusion partners are chosen to confer specific properties to the interferon antagonist such as the ability to dimerize or multimerize or the ability to traverse the blood-brain barrier.

In a preferred embodiment of the invention, interferon antagonists are fused to the human transferrin protein, e.g., Genbank accession number: XM_002793 which facilitates passage across the blood brain barrier (see "Modifications of Interferon Antagonist Proteins", infra).

In a preferred embodiment of the invention, interferon antagonists are dimers with an enhanced binding affinity for interferons. For example, human IFN-γ can be a dimer, and its interaction with the homodimer of IFN-γ ligand-binding subunits provides a significantly stronger bond than one subunit alone. This improvement in binding affinity has been demonstrated by Moosmayer and co-workers (Moosmayer, D. et al., 1995, J. Interferon. Cytokine Res. 15:1111-1115). An example of the human IFN-γ receptor fragment modified to form a dimer and further modified to enhance BBB transport via fusion to the human transferrin protein is presented in FIG. 6A.

5.2.3 Primers According to the Invention

The invention provides for oligonucleotide primers useful for amplifying interferon antagonist sequences, such as those cDNA sequences that encode the Vaccinia B8R or B18R proteins.

5.2.4 Primer Design

Primers may be selected manually by analyzing the template sequence. Computer programs, however, are also available in selecting primers to generate an amplified product with a designed length, e.g., primer premier 5 and primer 3.

It is known in the art that primers that are about 20-25 bases long and with 50% G-C content will work well at annealing temperature at about 52-58° C. These properties are preferred when designing primers for the subject invention. Longer primers, or primers with higher G-C contents, have annealing optimums at higher temperatures; similarly, shorter primers, or primers with lower G-C contents, have optimal annealing properties at lower temperatures. A convenient, simplified formula for obtaining a rough estimate of the melting temperature of a primer 17-25 bases long is as follows:

Melting temperature ($Tm$ in ° $C$.)=4×(# of $G$+# of $C$)+2×(# of $A$+# of $T$)

Shorter fragments are amplified more efficiently than longer fragments although target of more than 10 kb can be successfully amplified. Therefore preferably primers are selected so to amplify a relatively short product. Preferably, primers are selected to generate an amplified product of less than 500 bp, or 200 bp, or more preferably 100 bp in length or most preferably 73 bp in length.

In accordance with the preferred embodiments, optimal results have been obtained using primers, which are 19-25 in length. However, one skilled in the art will recognize that the length of the primers used may vary. For example, it is envisioned that shorter primers containing at least 15, and preferably at least 17, may be suitable. The exact upper limit of the length of the primers is not critical. However, typically the primers will be less than or equal to approximately 50 bases, preferably less than or equal to 30 bases.

5.2.5 Primer Synthesis

Methods for synthesizing primers are available in the art. The oligonucleotide primers of this invention may be prepared using any conventional DNA synthesis method, such as, phosphotriester methods such as described by Narang et al. (1979, Meth. Enzymol., 68:90) or Itakura (U.S. Pat. No. 4,356,270), or and phosphodiester methods such as described by Brown et al. (1979, Meth. Enzymol., 68:109), or automated embodiments thereof, as described by Mullis et al. (U.S. Pat. No. 4,683,202). Also see particularly Sambrook et al. (1989), Molecular Cloning: A Laboratory Manual (2d ed.; Cold Spring Harbor Laboratory: Plainview, N.Y.), herein incorporated by reference.

5.2.6 Vectors Useful According to the Invention

There is a wide array of vectors known and available in the art that are useful for the expression of interferon antagonists according to the invention. The selection of a particular vector clearly depends upon the intended use. For example, the selected vector must be capable of driving expression of the interferon antagonist or variant thereof in the desired cell type, whether that cell type be prokaryotic or eukaryotic. Many vectors comprise sequences allowing both prokaryotic vector replication and eukaryotic expression of operably linked gene sequences.

Vectors useful according to the invention may be autonomously replicating, that is, the vector, for example, a plasmid, exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors and in stably transfected cell lines. Vectors useful according to the invention preferably comprise sequences operably linked to an interferon antagonist protein coding sequences that permit the transcription and translation of fusion protein polynucleotide sequences. The term "transcriptional regulatory sequences" refers to the combination of a promoter and any additional sequences conferring desired expression characteristics (e.g., high level expression, inducible expression, tissue-or cell-type-specific expression) on an operably linked nucleic acid sequence. An "expression vector", according to the invention, comprises either an inducible promoter, or a tissue-specific promoter. A constitutive promoter such as viral promoters or promoters from mammalian genes, are generally active in promoting transcription. Examples of constitutive viral promoters include the HSV, TK, RSV, SV40 and CMV promoters, of which the CMV promoter is a currently preferred example. Examples of constitutive mammalian promoters include various housekeeping gene promoters, as exemplified by the β-actin promoter. Inducible promoters and/or regulatory elements are also contemplated for use with the expression vectors of the invention. Examples of suitable inducible promoters include promoters from genes such as cytochrome P450 genes, heat shock protein genes, metallothionein genes, hormone-inducible genes, such as the estrogen gene promoter, and the like. Promoters that are activated in response to exposure to ionizing radiation, such as fos, jun and egr-1, are also contemplated. The tetVP16 promoter that is responsive to tetracycline is a currently preferred example. Tissue-specific promoters are also contemplated for use with the expression vectors of the invention. Examples of such promoters that may be used with the expression vectors of the invention include promoters from the liver fatty acid binding (FAB) protein gene, specific for colon epithelial cells; the insulin gene, specific for pancreatic cells; the transphyretin, α1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells.

The selected promoter may be any DNA sequence that exhibits transcriptional activity in the selected host cell, and may be derived from a gene normally expressed in the host cell or from a gene normally expressed in other cells or organisms. Examples of promoters include, but are not limited to the following: prokaryotic promoters: *E. coli* lac, tac, or trp promoters, lambda phage PR or PL promoters, bacteriophage T7, T3, Sp6 promoters, *B. subtilis* alkaline protease promoter, and the *B. stearothermophilus* maltogenic amylase promoter, etc.; eukaryotic promoters: yeast promoters, such as GAL1, GAL4 and other glycolytic gene promoters (see for example, Hitzeman et al., 1980, J. Biol. Chem. 255: 2073-12080; Alber & Kawasaki, 1982, J. Mol. Appl. Gen. 1:419-434), LEU2 promoter (Martinez-Garcia et al., 1989, Mol. Gen. Genet. 217:464-470), alcohol dehydrogenase gene promoters (Young et al., 1982, in Genetic Engineering of Microorganisms for Chemicals, Hollaender et al., eds., Plenum Press, N.Y.), or the TPI1 promoter (U.S. Pat. No. 4,599,311); insect promoters, such as the polyhedrin promoter (U.S. Pat. No. 4,745,051; Vasuvedan et al., 1992, FEBS Lett. 311:7-11), the P10 promoter (Vlak et al., 1988, J. Gen. Virol. 69:765-776), the *Autographa californica* polyhedrosis virus basic protein promoter (EP 397485), the baculovirus immediate-early gene 1 promoter (U.S. Pat. Nos. 5,155,037 and 5,162,222), the baculovirus 39K delayed-early gene promoter (also U.S. Pat. Nos. 5,155,037 and 5,162,222) and the OpMNPV immediate early promoter 2; mammalian promoters: the SV40 promoter (Subramani et al., 1981, Mol. Cell. Biol. 1:854-864), metallothionein promoter (MT-1; Palmiter et al., 1983, Science 222: 809-814), adenovirus 2 major late promoter (Yu et al.,1984, Nucl. Acids Res. 12:9309-21), cytomegalovirus (CMV) or other viral promoter (Tong et al., 1998, Anticancer Res. 18:719-725), or even the endogenous promoter of a gene of interest in a particular cell type.

A selected promoter may also be linked to sequences rendering it inducible or tissue-specific. For example, the addition of a tissue-specific enhancer element upstream of a selected promoter may render the promoter more active in a given tissue or cell type. Alternatively, or in addition, inducible expression may be achieved by linking the promoter to any of a number of sequence elements permitting induction by, for example, thermal changes (temperature sensitive), chemical treatment (for example, metal ion-or IPTG-inducible), or the addition of an antibiotic inducing agent (for example, tetracycline).

Regulatable expression is achieved using, for example, expression systems that are drug inducible (e.g., tetracycline, rapamycin or hormone-inducible). Drug-regulatable promoters that are particularly well suited for use in mammalian cells include the tetracycline regulatable promoters, and glucocorticoid steroid-, sex hormone steroid-, ecdysone-, lipopolysaccharide (LPS)-and isopropylthiogalactoside (IPTG)-regulatable promoters. A regulatable expression system for use in mammalian cells should ideally, but not necessarily, involve a transcriptional regulator that binds (or fails to bind) non mammalian DNA motifs in response to a regulatory agent, and a regulatory sequence that is responsive only to this transcriptional regulator.

There are a number of well known bacteriophage-derived vectors useful according to the invention. Foremost among these are the lambda-based vectors, such as Lambda Zap II or Lambda-Zap Express vectors (Stratagene) that allow inducible expression of the polypeptide encoded by the insert. Others include filamentous bacteriophage such as the M13-based family of vectors.

A number of different viral vectors are useful according to the invention, and any viral vector that permits the introduction and expression of sequences encoding interferon antagonist polypeptides or variants thereof in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semiliki forest viral (alphaviral) vectors and Vaccinia viruses. Defective retroviruses are well characterized for use in gene transfer (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

In addition to retroviral vectors, Adenovirus can be manipulated such that it encodes and expresses a gene product of interest but is inactivated in terms of its ability to replicate in a normal lytic viral life cycle (see for example Berkner et al., 1988, BioTechniques 6:616; Rosenfeld et al., 1991, Science 252:431-434; and Rosenfeld et al., 1992, Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. For a review see Muzyczka et al., 1992, Curr. Topics in Micro. and Immunol. 158:97-129. An AAV vector such as that described in Traschin et al. (1985, Mol. Cell. Biol. 5:3251-3260) can be used to introduce nucleic acid into cells. A variety of nucleic acids have been introduced into different cell types using AAV vectors (see, for example, Hermonat et al., 1984, Proc. Natl. Acad. Sci. USA 81:6466-6470; and Traschin et al., 1985, Mol. Cell. Biol. 4:2072-2081).

The introduction and expression of foreign genes is often desired in insect cells because high level expression may be obtained, the culture conditions are simple relative to mammalian cell culture, and the post-translational modifications made by insect cells closely resemble those made by mammalian cells. For the introduction of foreign DNA to insect cells, such as *Drosophila* S2 cells, infection with baculovirus vectors is widely used. Other insect vector systems include, for example, the expression plasmid pIZ/V5-His (In Vitrogen, San Diego, Calif., USA) and other variants of the pIZ/V5 vectors encoding other tags and selectable markers. Insect cells are readily transfectable using lipofection reagents, and there are lipid-based transfection products specifically optimized for the transfection of insect cells (for example, from Pan Vera (Madison, Wis., USA)).

5.2.7 Host Cells Useful According to the Invention

Any cell into which recombinant vectors carrying an interferon antagonist gene or variant thereof may be introduced and wherein the vectors are permitted to drive the expression of interferon anatagonist protein sequences is useful according to the invention. Vectors suitable for the introduction of interferon anatagonist protein-encoding sequences in host cells from a variety of different organisms, both prokaryotic and eukaryotic, are described herein above or known to those skilled in the art.

Host cells may be prokaryotic, such as any of a number of bacterial strains, or may be eukaryotic, such as yeast or other fungal cells, insect or amphibian cells, or mammalian cells including, for example, rodent, simian or human cells. Cells expressing interferon anatagonist proteins of the invention may be primary cultured cells, for example, primary human fibroblasts or keratinocytes, or may be an established cell line, such as NIH3T3, 293T or CHO cells. Further, mammalian cells useful for expression of interferon anatagonist proteins of the invention may be phenotypically normal or oncogenically transformed. It is assumed that one skilled in the art can readily establish and maintain a chosen host cell type in culture.

5.2.8 Antibodies According to the Invention

The invention provides for antibodies directed to different interferons. Antibodies can be made using standard protocols known in the art (see, for example, Antibodies: A Laboratory Manual ed. by Harlow and Lane (Cold Spring Harbor Press: 1988)). A mammal, such as a mouse, hamster, or rabbit can be immunized with an immunogenic form of the interferon. Immunogens for raising antibodies are prepared by mixing the polypeptides (e.g., isolated recombinant polypeptides or synthetic peptides) with adjuvants. Alternatively, interferon proteins or peptides are made as fusion proteins to larger immunogenic proteins. Polypeptides can also be covalently linked to other larger immunogenic proteins, such as keyhole limpet hemocyanin. Alternatively, plasmid or viral vectors encoding interferon polypeptide or interferon peptides can be used to express the polypeptides and generate an immune response in an animal as described in Costagliola et al., 2000, J. Clin. Invest. 105:803-811, which is incorporated herein by reference in its entirety. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies (Fv, Fab, scFV, F(ab)$_2$, VH, VL). In a preferred embodiment, the immunogen is administered to rabbits.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with interferon polypeptide or peptides, and monoclonal antibodies isolated from the media of a culture comprising such hybridoma cells.

The term "antibody" as used herein is intended to include antibody fragments, which are also specifically reactive with one of the subject polypeptides or peptides of the invention. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanized molecules having affinity for a polypeptide or peptide of the invention conferred by at least one CDR region of the antibody. In preferred embodiments, the antibody further comprises a label attached thereto and able to be detected, e.g., the label can be a radioisotope, fluorescent compound, chemiluminescent compound, enzyme, or enzyme co-factor.

Antibodies can be used, e.g., to monitor protein levels in an individual for determining, e.g., whether a subject has a immune disease or condition, that is associated with an aberrant amount of peptide in tissue biopsies or allowing determination of the efficacy of a given treatment regimen for an individual afflicted with such a disorder. The level of the interferons of the invention may be measured in bodily fluids, such as in blood samples. Another application of antibodies of the present invention is in the immunological screening of bioavailable interferon in the blood samples of patients afflicted with a disease to be treated as disclosed herein. In another embodiment of the invention, the anti-interferon antibody is an interferon antagonist.

5.2.9 Interferon Antagonist Protein Expression

In order to express a biologically active protein, the nucleotide sequence encoding the protein of interest or its functional equivalent, is inserted into an appropriate expression vector, i.e., a vector which contains the necessary elements for the transcription and translation of the inserted coding sequence. The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. Methods which are well known to those skilled in the art can be used to construct expression vectors containing a protein-encoding sequence and appropriate transcriptional or translational controls. These methods include in vivo recombination or genetic recombination. Such techniques are described in Ausubel et al., supra and Sambrook et al., supra.

A variety of expression vector/host systems may be utilized to contain and express a protein product of a candidate gene according to the invention. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vector (e.g., cauliflower mosaic virus, CaMV; tobacco mosaic virus, TMV) or transformed with bacterial expression vectors (e.g., Ti or pBR322 plasmid); or animal cell systems.

In bacterial systems, a number of expression vectors may be selected depending upon the use intended for the protein of interest. For example, when large quantities of a protein are required for the production of antibodies, vectors which direct high level expression of fusion proteins that are readily purified may be desirable. Such vectors include, but are not limited to, the multifunctional *E. coli* cloning and expression vectors such as Bluescript® (Stratagene, La Jolla, Calif., USA), in which the sequence encoding the protein of interest may be ligated into the vector in frame with sequences encoding the amino-terminal Met and the subsequent 27 residues of β-galactosidase so that a hybrid protein is produced; pIN vectors (Van Heeke & Schuster, 1989, J. Biol. Chem. 264:5503); and the like. Pgex vectors (Promega, Madison, Wis., USA) may also be used to express foreign polypeptides as fusion proteins with GST. In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al. (supra) and Grant et al., 1987, Methods in Enzymology 153:516.

In cases where plant expression vectors are used, the expression of a sequence encoding a protein of interest may be driven by any of a number of promoters. For example, viral promoters such as the 35S and 19S promoters of CaMV (Brisson et al., 1984, Nature 310:511) may be used alone or in combination with the omega leader sequence from TMV (Takamatsu et al., 1987, EMBO J. 6:307). Alternatively, plant promoters such as the small subunit of RUBISCO (Coruzzi et al., 1984, EMBO J. 3:1671; Broglie et al., 1984, Science, 224:838); or heat shock promoters (Winter J. and Sinibaldi R. M., 1991, Results Probl. Cell. Differ. 17:85) may be used. These constructs can be introduced into plant cells by direct DNA transformation or pathogen-mediated transection. For reviews of such techniques, see Hobbs S. or Murry L. E. in McGraw Hill Yearbook of Science and Technology (1992) McGraw Hill New York N.Y., pp 191-196 or Weissbach and Weissbach (1988) Methods for Plant Molecular Biology, Academic Press, New York, pp 421-463.

An alternative expression system which could be used to express a protein of interest is an insect system. In one such system, *Autographa californica* nuclear polyhedrosis virus (AcNPV) is used as a vector to express foreign genes in *Spodoptera frugiperda* cells or in *Trichoplusia* larvae. The sequence encoding the protein of interest may be cloned into a nonessential region of the virus, such as the polyhedrin gene, and placed under control of the polyhedrin promoter. Successful insertion of the sequence encoding the protein of interest will render the polyhedron gene inactive and produce recombinant virus lacking coat protein coat. The recombinant viruses are then used to infect *S. frigoerda* cells or *Trichoplusia* larvae in which the protein of interest is expressed (Smith et al., 1983., J. Virol. 46:584; Engelhard et al., 1994, Proc. Nat. Acad. Sci. USA 91:3224).

In mammalian host cells, a number of viral-based expression systems may be utilized such as vaccinia virus, adenoviruses and retroviruses and the like. In cases where an adenovirus is used as an expression vector, a sequence encoding the protein of interest may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk, 1984, Proc. Natl. Acad. Sci. USA 81:3655). In addition, transcription enhancers, such as the rous sarcoma virus (RSV) enhancer, may be used to increase expression in mammalian host cells.

Specific initiation signals may also be required for efficient translation of a sequence encoding the protein of interest. These signals include the ATG initiation codon and adjacent sequences. In cases where the sequence encoding the protein, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf et al., 1994, Results Probl. Cell. Differ., 20:125; Bittner et al., 1987, Methods in Enzymol. 153:516). In addition, a host cell strain may be chosen for its ability to modulate the expression of the inserted sequences or to process the expressed protein in the desired fashion. Such modifications of the polypeptide include but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express a foreign protein may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clumps of stably transformed cells can be expanded using tissue culture techniques appropriate to the cell type.

Any number of selection systems may be used to recover transformed cell lines. These include, but are not limited to, the herpes simplex virus thymidine kinase (Wigler et al., 1977, Cell 11:223) and adenine phosphoribosyltransferase (Lowy et al., 1980, Cell 22:817) genes which can be employed in tk- or aprt-cells, respectively. Also, antimetabolite, antibiotic or herbicide resistance can be used as the basis for selection; for example, dhfr which confers resistance to methotrexate (Wigler et al., 1980, Proc. Natl. Acad. Sci. USA 77:3567); npt, which confers resistance to the aminoglycosides neomycin and G-418 (Colbere-Garapin et al., 1981, J. Mol. Biol., 150: 1) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman and Mulligan, 1988, Proc. Natl. Acad. Sci. 85:8047). Recently, the use of visible markers has gained popularity with such markers as anthocyanins, B glucuronidase and its substrate, GUS, and luciferase and its substrate, luciferin, being widely used not only to identify transformants, but also to quantify the amount of transient or stable protein expression attributable to a specific vector system (Rhodes et al., 1995, Methods. Mol. Biol. 55:121).

5.2.10 Modifications of Interferon Antagonist Proteins

When needed, the IFN binding proteins, and their formulation, can be modified. Such modifications are intended to fall within the scope of the present invention, and examples are provided below.

5.2.10.1 Multimerization

For various reasons that include increasing IFN binding affinity and/or beneficially altering metabolism and excretion, the IFN binding proteins can be linked together as homomultimers (e.g., as in FIG. 6A) or as heteromultimers (e.g., as in FIG. 6B) for example by cysteine bridges (Moosmayer, D. et al., 1995, J. Interferon Cytokine Res. 15:1111-1115), other protein-protein interactions, and/or as fusion proteins coded for by linked genes. These general procedures are well known to those practiced in the art.

5.2.10.2 Blood Brain Barrier (BBB) Transport Enhancement

For the treatment of some diseases it may be desirable or necessary to enhance the ability of the interferon binding proteins to pass through the BBB. This can be accomplished by various modifications described in the literature (Poduslo, J. F. et al., 1994, Brain Res. Mol. Brain Res. 23:157-162; Triguero, D. et al., 1989, Proc. NatI. Acad. Sci. USA 86:4761-4765), e.g., catonization (Triguero, D. et a!., 1991, J. Pharmacol. Exp. Ther. 258:186-192) or glycation (Poduslo, J. F. et a!., 1994, Brain Res. Mol Brain Res. 23:157-162) including linkage as a fusion protein with an iron binding/transport protein (e.g., p97 (U.S. Pat. No. 5,981, 194). The ability of transferrin to enhance the BBB uptake of other proteins has been taught by others (Shin, S. U. et al., 1995, Proc. Nati. Acad. Sci. USA 92:2820-2824). The use of human transferrin (Tf) to enhance the ability of a specific group of polypeptides to pass through the blood-brain barrier (BBB) is taught by U.S. Pat. Nos. 5,672,683, 5,182,107 and 5,527,527. The Tf polypeptide can be added to the fusion proteins of the present invention using standard procedures using, for example the Tf gene obtained from a human liver cDNA library (Clontech, Palo Alto, Calif., USA) using the following primers and standard procedures:

```
P1: TCTAGATGGTGTGCAGTGTCGGAGC      (SEQ ID NO: 3)

and

P2: CGTACGGAAAGTGCAGGCTTCCAG.      (SEQ ID NO: 4)
```

FIG. 6 presents examples of interferon binding proteins as fusion proteins with human transferrin along with the further modification of linkage through a flexible hinge region. A specific immunoglobin example of this type of linkage is described by Michaelsen et al. (Michaelsen, T. E. et al., 1977, J. Biol. Chem. 252:883-889).

5.2.10.3 Reducing Immunogenicity and Improving Phamacokinetics

Additional modifications could, for example, include addition of polyethylene glycol (PEG) and/or other moieties (Hershfield, M. S. et al., 1991, Proc. Natl. Acad. Sci. USA. 88:7185-7189). This modification has been shown to reduce the ability of the immune system to mount an immune response (Hershfield, M. S. et al., 1991, Proc. Natl. Acad. Sci. USA 88:7185-7189) and to increase serum half-life partly by increasing overall molecule size.

5.2.10.4 Modification for Alternate Modes of Administration

Polyethylene glycol (PEG) and other functionally similar molecules can also be used as part of the formulation to provide the advantage of time-release and/or reduced site of injection inflammation (Hershfield, M. S. et al., 1991, Proc. Natl. Acad. Sci. USA 88:7185-7189; Somack, R. et al., 1991, Free Radic. Res. Commun. 12-13:553-562). Other examples of modifications would include preparation as an aerosol for transpulmonary delivery (U.S. Pat. No. 5,558, 085) modifications for oral delivery (U.S. Pat. No. 6,153, 211) and/or modifications to improve intravenous (IV), subcutaneous (SC), nasal, or intramuscular (IM) routes of delivery.

5.3. Selection of Dose and Timing of Administration 5.3.1 Dosage, Formulation and Administration The therapeutic agent of the invention can be used in a composition that is combined with a pharmaceutically acceptable carrier. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The composition may also contain other agents, which either enhance the activity of the composition, or compliment its activity or use in treatment, or maintain the activity of the therapeutic agent in storage. Such additional factors and/or agents may be included in the composition to produce a synergistic effect or to minimize side effects. Additionally, administration of the composition of the present invention may be administered concurrently with other therapies.

Administration of the therapeutic agent of the present invention can be carried out in a variety of conventional ways, such as oral ingestion, inhalation, topical application or cutaneous, subcutaneous, intraperitoneal, parenteral or intravenous injection.

The compositions containing the therapeutic agent of the present invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier or vehicle.

Modes of administration of the therapeutic agent of the present invention include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents, and/or compounds to shield the immunogenic determinant of the therapeutic agent. Prevention of the action of microorganisms may be improved by the inclusion of various antibacterial and antifungal agents such as paraben, chlorobutanol, phenol sorbic acid and the like. It may also be desirable to include isotonic agents such as sugars, sodium chloride and the like. Prolonged absorption of an injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose dose or multi-dose containers. Extemporaneous injection solutions and suspensions may be prepared from sterile powders, granules and tablets of the kind previously described.

When a therapeutically effective amount of the therapeutic agent of the present invention is administered orally, the composition of the present invention will be in the form of a tablet, capsule, powder, solution or elixir. When administered in tablet form, the composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the composition may further contain physiological saline solution, dextrose or other saccharide solution, or glycols such as ethylene glycol, propylene glycol or polyethylene glycol. When administered in liquid form, the composition contains from about 0.5 to 90% by weight of protein of the present invention, and preferably from about 1 to 50% protein of the present invention.

When a therapeutically effective amount of the therapeutic agent of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The composition of the present invention may also contain stabilizers, preservatives, buffers, antioxidants, or other additives known to those of skill in the art.

Topical administration, in which the composition is brought in contact with tissue(s), may be suitable for sarcoidosis of the skin. By "contacting" is meant not only topical application, but also those modes of delivery that introduce the composition into the tissues, or into the cells of the tissues.

Use of timed release or sustained release delivery systems are also included in the invention. Such systems are highly desirable in situations where the patient is debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The amount of the therapeutic agent of the present invention in the pharmaceutical composition of the present invention will depend upon the nature and severity of the condition being treated, and on the nature of prior treatments, which the patient has undergone. Ultimately, the attending physician will decide the amount of the therapeutic agent of the present invention with which to treat each individual patient. Initially, the attending physician will administer low doses of the therapeutic agent of the present invention and observe the patient's response. Larger doses of may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the therapeutic agent of the present invention will be in the range of 12 to 24 hours of continuous intravenous administration. Ultimately the attending physician will decide on the appropriate duration of intravenous therapy using the pharmaceutical composition of the present invention.

The amount of an antibody antagonist administered is between 1 and 100 mg/kg. The preferred route of administration of an antibody antagonist is intravenous administration to infant and adult subjects. The preferred route of administration to fetal subjects is by intravenous administration to the mother followed by transplacental transport. Alternatively antibody antagonists can be administered by intramuscular and subcutaneous routes. When an antagonist is delivered transplacentally, the calculation of the dose is based on the maternal weight.

The antagonist is administered to patients having Down syndrome preferably at the time when the central nervous system is developing most rapidly. The preferred period of administration is from a gestational age of 24 weeks onwards until a post natal age of about 2 years. Even though some proliferation of neurons takes place during weeks 8-18, it is not critical that an antagonist be administered to a human subject prior to week 20-24 of gestational age because the synaptic connections between the neurons are not formed until week 20. Brandt, I., 1981, J. Perinat. Med. 9:3. The administration of the antagonist to patients having Alzheimer's disease should commence at the time that the diagnosis of probable Alzheimer's disease is first made and continue there after. In middle age, subjects having Down syndrome develop a dementia having an anatomical pathology which is identical to Alzheimer's disease (Mann, D. M. A., 1988, Mech. Aging and Develop. 43:99-136). Thus, the administration of the antagonist to Down syndrome patients can be continued throughout the life of the patient, as Down syndrome patients are at risk for Alzheimer's disease ab initio.

The frequency of administration is determined by the circulation time of the antagonist, which can be determined by direct measurement by methods well known to those skilled in the art.

In an alternative embodiment of the invention, the administration of interferon antagonists is replaced by the extracorporeal treatments of the subject's blood to remove circulating interferon, such as is described in U.S. Pat. No. 4,605,394.

5.3.2 Diseases to be Treated by Interferon Antagonists of the Invention

Appropriate pharmacological preparations of the compositions of the present invention are useful for the treatment and prevention of diseases where increased synthesis of, or responsivity to, the interferons is involved. Examples of these are Down syndrome, Alzheimer's disease, HIV infection, autoimmune disease, transplant rejection, and infant encephalitis.

5.3.2.1 Down's Syndrome:

The tissues of a Down syndrome individual displays increased responsivity to both IFN-γ and IFN-α. In addition, there exist significant similarities between the side effects of interferon therapy and Down syndrome pathologies (Maroun, L. E. et al., 1998, Down syndrome: Research and Practice 5:143-147; U.S. Pat. No. 5,780,027).

5.3.2.2 Alzheimer's Disease

The presence of trisomy 21 (Down syndrome) cells (Geller, L. N. et al., 1999, Neurobiol. Dis. 6:167-179) and an increase in interferon levels (Yamada, T. et al., 1994, Neurosci. Lett. 181:61-64) are both reported to be present in the Alzheimer's disease brain. Further, the interferons are involved in both the synthesis and the processing of a brain protein (APP) that plays a central role in the development and progression of AD associated dementia (Blasko, I. et al., 1999, Faseb. J. 13:63-68).

5.3.2.3 HIV Infection

Increased levels of both IFN-γ and IFN-α have been demonstrated in HIV infected patients of various ages (Fuchs, D. et al., 1989, J. Acquir. Immune Defic. Syndr. 2:158-162; Minagawa, T. et al., 1989, Life Sci. 45:iii-vii; Rossol, S. et al., 1989, J. Infect. Dis. 159:815-821). Clinical data suggests that decreasing the IFN activity improves the HIV infected patient's prognosis (Fall, L. S. et al., 1995, Biomed. Pharmacother. 49:422-428; Gringeri, A. et al., 1994, J. Acquir. Immune Defic. Syndr. 7:978-988.; Gringeri, A. et al., 1995, Cell Mol. Biol. (Noisy-le-grand) 41:381-387; Gringeri, A. et al., 1996, J. Acquir. Immune Defic. Syndr. Hum. Retrovirol. 13:55-67.; Gringeri, A. et al., 1999, J. Acquir. Immune Defic. Syndr. Hum. Retrovirol. 20:358-370). The method used these studies is taught by U.S. Pat. No. 6,093,405. This method is both unreliable (Fall, L. S et al., 1995, Biomed. Pharmacother. 49:422-428; Gringeri, A. et al., 1994, J. Acquir. Immune Defic. Syndr. 7:978-988; Gringeri, A. et al., 1995, Cell Mol. Biol. (Noisy-le-grand) 41:381-387; Gringeri, A. et al., 1996, J. Acquir. Immune Defic. Syndr. Hum. Retrovirol. 13:55-67; Gringeri, A. et al., 1999, J. Acquir. Immune Defic. Syndr. Hum. Retrovirol. 20:358-370) and irreversible.

Administration of the pharmacological compositions described herein is a significant improvement in this method as it provides for predictable and controllable IFN antagonist levels that can be adjusted according to patient needs and treatment can be discontinued in the event IFN activity falls below safe levels.

5.3.2.4 Encephalitis in Infants

Encephalitis in infants can be caused by viral infection (e.g., herpes infection (Dussaix, E. et al., 1985, Acta Neurol. Scand. 71:504-509) or have unknown origin (e.g., Aicardi-Goutieres Syndrome (Akwa, Y. et al., 1998, J. Immunol. 161:5016-5026). Both of these conditions are associated with increased levels of IFN (Akwa, Y. et al., 1998, J. Immunol. 161:5016-5026; Dussaix, E. et al., 1985, Acta Neurol. Scand. 71:504-509). In the case of Aicardi-Goutieres Syndrome and animal models of it, elevated levels of IFN may be the primary cause of the disease.

5.3.2.5 Autoimmune Disease

Elevated IFN levels play a central role in the development and progression of various autoimmune diseases (Le Page, C. et al., 2000, Rev. Immunogenet. 2:374-386). Thus, it is expected that individuals suffering from these diseases would benefit by use of the present invention.

5.3.2.6 Transplant Rejection

Interferon has been shown to play an important role in the immunological rejection of transplanted cells, tissues and/or organs (see, Cytokines and Autoimmunity, O'Shea, J. J., Ma, A., Lipsky, P., Nature Rev. Immunol. 2(1):37-45 (2002)). Thus, it is expected that individuals suffering from these diseases would benefit by use of the present invention.

The above descriptions are by example only and are not intended to limit the present invention's usefulness. Indeed it is immediately obvious to one skilled in the art that in IFNs play an important role in various other diseases. These diseases are considered to be within the scope of the present invention. The described compositions would be useful for the treatment of all diseases where interferon hyper-production or hyper-responsivity is involved. Alzheimer's disease, HIV infection, Down syndrome, autoimmune disease, and infant encephalitis are examples of such diseases.

5.3.3 Animal Models of the Diseases to be Treated According to the Invention

Animal models of disease are useful for determining the efficacy of treatment using the pharmaceutical compositions according to the invention. For example, an animal model for multiple sclerosis is experimental autoimmune encephalomyelitis (EAE), which can be induced in a number of species, e.g., guinea pig (Suckling et al., 1984, Lab. Anim. 18:36-39), Lewis rat (Feurer et al., 1985, J. Neuroimmunol. 10:159-166), rabbits (Brenner et al., 1985, Isr. J. Med. Sci. 21:945-949), and mice (Zamvil et al., 1985, Nature 317: 355-358).

There are numerous animal models known in the art for diabetes, including models for both insulin-dependent diabetes mellitus (IDDM) and non-insulin-dependent diabetes mellitus (NIDDM). Examples include the non-obese diabetic (NOD) mouse (e.g., Li et al., 1994, Proc. Natl. Acad. Sci. USA. 91:11128-11132), the BB/DP rat (Okwueze et al., 1994, Am. J. Physiol. 266:R572-R577), the Wistar fatty rat (Jiao et al., 1991, Int. J. Obesity 15:487-495), and the Zucker diabetic fatty rat (Lee et al., 1994, Proc. Natl. Acad. Sci. USA. 91:10878-10882). There are also animal models for autoimmune thyroiditis (Dietrich et al., 1989, Lab. Anim. 23:345-352) and Crohn's disease (Dieleman et al., 1997, Scand. J. Gastroenterol. Supp. 223:99-104; Anthony et al., 1995, Int. J. Exp. Pathol. 76:215-224; Osborne et al., 1993, Br. J. Surg. 80:226-229).

Some representative animals models are included below.

Down Syndrome:
Trisomy 16 mouse: Gropp, A. et al., Cytogenet. Cell Genet. 14:42-62 (1975)
Partial trisomy 16 mouse: Davisson, M. T. et al. Prog. Clin. Biol. Res. 384:117-133 (1993)

Alzheimer's Disease:
Transgenic mice expressing beta-amyloid precursor protein [Games, D. et al., Nature, 9:373(6514):523-7(1995)]

Pathology of HIV Infection:
Retrovirus infected mice: Morse III, H. C. et al., AIDS 6:607-621 (1992)
Retrovirus infected cats: Podell, M. et al., J. Psychopharmacol. 14(3):205-213 (2000)
Retrovirus infected monkeys: Rausch, D. M. et al., J. Leukoc. Biol. 65(4):466-474(1999)
Intracerebral HIV coat protein injection in rats: Glowa, J. R. et al., Brain Res. 570:49-53(1992)

Encephalitis in Infants:
Infantile encephalitis (Aicardi-Goutieres syndrome): IFN-α transgenic mice: Akwa, Y. et al., J. Immuno. 161:5016-5026 (1998)
Mouse Herpes simplex virus encephalitis: Mayding-Lamade, U. et al., Neurosci. Lett. 22; 248(I):13-16 (1998)
LCM virus encephalitis in mice: Pfau, C. J. et al., J. Gen. Virol. 64(8):1827-1830 (1993)

Autoimmune Disease:
Diabetes: IFN-α transgenic mice [Steward, T. A. et al., Science 260:1942-46 (1993)
Systemic Lupus Erythematosus: NZB/W F1 mice: Jacob, C. O. et al., J. Exp. Med. 166(3):798-803 (1987)
Multiple Sclerosis: IFN-γ Transgenic mice: Corbin, J. G. et al., Mol. Cell. Neurosci. 7(5):354-370 (1996)

Transplant Rejection:
Canine renal allografts: Fuller, L. et al., Tissue Antigens 43:163-169 (1994)

These accepted animal model systems, or others known and accepted in the art to be representative of human disease, can be used to test the efficacy of therapeutic approaches using the interferon antagonist polypeptides and variants thereof according to the invention. Generally, this is accomplished by administering the polypeptide composition to an animal that has or can be induced to have the model disease corresponding to the human disease one aims to treat, and monitoring the disease status. The response to the administered composition is then monitored by measuring the amount of bioavailable interferon on the bloodstream using anyone of a number of immunological assays known in the art such ELISA or radioimmunoassays and the like. Disease status is monitored according to criteria established for the particular disease or disease model, and treatment is considered effective if one or more symptoms or markers of disease are decreased by 10% or more relative to animals not treated or relative to the same animal before treatment.

5.4. Model Embodiment of the Invention

One embodiment of the invention is exemplified and its operability is demonstrated by the experiments that are presented in Example 1 below. Briefly, normal female mice were crossed with double heterozygous males having Rb(6.16) and Rb(16.17) chromosomes. The females were injected with a mixture of rat monoclonal anti-IFN-γ (1500 neutralizing units) and rabbit polyclonal anti-IFN-α/β (1362 neutralizing units) interperitonally (i.p.) on days 8, 10, 12 and 14 of pregnancy. On day 17 the embryos were biopsied for cytogenetic classification, sacrificed and four gross parameters were measured and compared to the genetically normal littermates in order to assess relative development. Control groups consisted of untreated females and sham treated females which were given normal rabbit and rat serum γ globulin injections.

The four measured parameters were overall (crown-rump) length of the fetus, shape of the back (normally concave at birth), eye-closing (the eyes normally close shortly before birth) and fetal weight. The results of the comparison of each of the parameters from 17 untreated, 16 sham treated and 18 treated controls showed a statistically significant reduction in the growth retardation/maturation of the treated trisomy-16 fetal mice compared to their euploid littermates.

The fetuses from anti-IFN treated mothers had a mean weight decrease of −10.92% compared to a −21.47% decrease for the uninjected group (p=0.079) and a −30.46% decrease for the ns-IgG injected group (p=0.0003) relative to diploid littermates. The uninjected and ns-IgG injected control groups were not statistically different from each other (p=0.174).

6. EXAMPLE TREATMENT OF MURINE TRISOMY-16 BY A INTERFERON ANTAGONIST

6.1. Materials and Methods

Animals and Mating. 6:16 Robertsonian translocation male (Rb[6.16]24Lub) and 17:16 Robertsonian translocation female (Rb[16.17]7Bnr) homozygotes were purchased from Jackson Laboratories, Bar Harbor, Me., USA. Mature (54 day) male offspring of these homozygotes (double heterozygotes) were mated to 8-10 wk old euploid, nulliparous, C3H/HeJ females (Jackson Laboratories). Surgery was performed on day 17 or 18 to yield fetuses at the 17-25 mm stage (Theiler, K. (1972) In: The House Mouse, Springer, Berlin, Heidelberg, N.Y.). The last three days of gestation are when the morphologic characteristics (eye closure, back curvature and accelerated growth) can be quantified.

Injections. Intraperitoneal (IP) injections (0.25 cc) were begun on post-coitus day 8 (implantation occurs on day 5.5). Injections were given every 48 hours for a total of four injections per animal.

Rabbit polyclonal anti-mouse α/β IFN purified IgG (970 neutralizing units/mg of protein, cat. #25301), and rat monoclonal IgG1 anti-mouse γ IFN, (7,200 neutralizing units/mg, cat. #25001) were obtained from Lee Biomolecular Research Incorporated, San Diego, Calif. The anti-IFNs (supplied lyophilized from saline) were dissolved in sterile water-for-injection (Investage) at a concentration that would deliver 1500 neutralizing units of anti-γ and 1362 neutralizing units of anti-α/β IgG per injection. The expectation was that the IgG would reach the developing fetus through active IgG placental transfer (Guzman-Enriques, L. et al., 1990, J. Rheumatol., 17:52-56). Control injections delivered the same mg quantities of rat (Pierce Chemical Co., Rockford, Ill., USA, Cat. #31233X) and rabbit (Pierce Chemical Co., Rockford, Ill., USA, Cat. #31207X) non-specific IgGs in an equivalent volume of sterile saline-for-injection (Abbott). A second control group consisted of uninjected mothers which were left undisturbed.

Fetus Processing. Fetuses, obtained by hysterectomy of mice sacrificed by cervical dislocation, were photographed, measured and fixed whole in Bouins fixative (Luna, L. G. (1968) In: Manual of Histologic Staining Methods of the Armed Forces Institute of Pathology, (3rd edition). The Blakiston Division, McGraw-Hill Book Company, New York). Prior to fixation, limb tissue was obtained and minced to provide fibroblast cultures for karyotyping. The fetal fibroblasts from the minced tissue were grown at 37° C. in EAGLE's Minimum Essential Media containing 20% fetal bovine serum, 2 mM glutamine, 100 units/ml of penicillin, and 100 µg/ml of streptomycin. After five days in culture, colchicine (Sigma Chemical Co., St. Louis, Mo., USA) was added to level of 1 µg/ml. One hour later, cells were collected, swelled in 25% media, and fixed in fresh methanol:acetic acid (3:1). Crown-to-rump length was measured immediately after the fetus was obtained by measuring the vertex-to-rump distance (without pressure on the fetus) while the fetus was floating in serum-free Minimum Essential Media. Except where otherwise noted, all statistical analyses were done using a two-tailed student's T-test.

6.2. Results and Discussion

Mice pregnant with trisomy 16 conceptuses were obtained by the mating of euploid nulliparous C3H/HeJ females with doubly heterozygous males. The males were also functionally euploid (i.e., they have a total of 40 chromosome arms) but they carried two Robertsonian translocation chromosomes (6.16 and 17.16), each with one chromosome #16 arm. The meiotic misdistribution of these translocation chromosomes results in a high frequency of trisomy 16 fetuses carrying a maternal acrocentric chromosome 16 and both paternal translocation pseudometacentric chromosomes. This genetic system has been described in detail (Gropp, A. et al., 1975, Cytogenet. Cell Genet. 14:42-62; Gearhart, J. D. et al., 1986, Brain Res. Bull. 16:789-801). Anti-IFN treated mothers received four IP injections of a cocktail of anti-α, β and γ IFN immunoglobulins. One control group of mothers was left unhandled and one was given comparable injections of non-specific IgG.

Mechanisms for the transfer of the IgG from mother-to-fetus and neonate vary widely from species to species. Generally, some combination of passive and active transport is involved; sequentially utilizing the yolk sac and placenta prior to birth, and the intestine postnatally. In the mouse system, maternal antibodies can initially be found in the fluid filling the blastocyst cavity (Brambell, F. W. R., 1966, The Lancet 7473). This may be due simply to passive diffusion, as this fluid generally resembles dilute maternal blood plasma. Shortly thereafter active transport of IgG class immunoglobulins via Fc receptors becomes primarily the function of the yolk sac. This function is later shared but, in rodents, never dominated by Fc mediated transfer of IgG across the placenta (Roberts, D. M. et al., 1990, J. Cell Biol. 111:1867-1876). In the experiments presented here, mice were injected after day 5.5 because of the possibility that trophoblast interferon may play an important role at implantation (Roberts, R. M., 1991, BioEssays 13:121-126). In the mouse, injected polyclonal rabbit IgG has an expected half-life of approximately 5 days (Spiegelberg, H. L. & W. O. Weigle, 1965, J. Exp. Med. 121:323-337).

A total of 68 late stage fetuses with abnormal morphology were obtained from among 440 offspring of 143 doubly heterozygous male×C3H/HeJ female matings. Only fetuses that were both successfully karyotyped and from litters where euploid fetuses averaged greater than 17 mm in length (crown-to-rump [CRL]) are included in Table 3 and in all graphs. Fifty-one of a total of 68 trisomies met these criteria. In all cases, the return-toward-normal values are seen with or without the inclusion of unkaryotyped fetuses. For comparison, p values calculated with the unkaryotyped fetuses included are provided in brackets next to those calculated using only successfully karyotyped fetuses.

Growth Retardation. The growth retardation seen in the trisomy 16 fetus is quite variable. Nonetheless, the trisomic fetuses from the anti-IFN treated mothers showed a significant return-toward-normal growth when CRL length is plotted against the average length of the euploid littermates (FIG. 1). This analysis suggests that unlike the erratic growth of their counterparts from untreated mothers, the trisomy 16 fetuses from anti-IFN treated mothers were nearly keeping pace with the growth of their euploid littermates.

On average the trisomic fetuses from anti-IFN treated mothers showed a 5.6% decrease in length compared to a 15.28% decrease for the fetuses from non-specific IgG injected mothers (p=0.014 [0.0009]) and a 14.59% decrease for the fetuses from uninjected mothers (p=0.015 [0.010]). The two control groups were not statistically different from each other (p=0.879 [0.759]). The improvement in growth was seen consistently against both control groups and in all the fetus size groups (17-20 mm, 20-23 mm, >23 mm, Table 3).

A similar return-toward-normal growth was observed when the decrease in trisomy 16 fetal weights were analyzed. The fetuses from anti-IFN treated mothers had a mean weight decrease of −10.92% compared to a −21.47% decrease for the uninjected group (p=0.079 [0.095], NS) and a −30.46% decrease for the ns-IgG injected group (p=0.0003 [0.0026]). The two control groups were not statistically different from each other (p=0.174 [0.33]).

There were no detectable effects of the non-specific IgG or anti-IFN injections on the euploid fetuses. Growth of each trisomic fetus was measured against its normal littermates to avoid errors due to a missed estimate of gestational age. In these matings, the mean normal littermate length (MNLL) measured 17.17 mm CRL at gestational day 16.5, 19.39 mm CRL at day 17.5 and 23.94 mm CRL at day 18.5 (plug date=day 0.5 [Kaufman' 92]). There was no significant difference between the MNLL of the uninjected control group (gestational day) 18.5 (MNLL=23.944 [N=18, p=0.419]) or the IgG injected control group (MNLL=23.75 [N=6, p=0.706]), and the anti-IFN treated group (MNLL=23.333 [N=24]). There was also no significant difference between the MNLL of the two control groups (p=0.826).

Eye Opening. Eye opening comparisons (FIG. 2A) were limited to fetuses from litters 17 mm to 23 mm in length. Prior to this stage all fetuses have open eyes. The eyes of fetuses from litters measuring 16.9-22.6 mm CRL obtained from anti-IFN treated mothers (N=13, mean=0.21 mm) had made significantly more progress toward closure than the eyes of comparably staged fetuses from untreated (N=11, mean=0.42 mm, p=0.019 [0.010]) and non-specific IgG injected mothers (N=11, mean=0.40 mm, p=0.026 [0.046]). There was no significant difference in the eye openings of the uninjected and non-specific IgG injected control groups (p=0.746 [0.300]). Progress toward eye closure may be an all or nothing event. Thus, it may be equally significant that 7 of the 13 fetuses (54%) from anti-IFN treated mothers had eye openings that averaged less than 0.2 mm compared to 2 of 11 (18%) of those from untreated mothers and 2 of 11 (18%) of the comparable fetuses from non-specific IgG treated mothers.

There have been numerous mutations detected in the mouse that lead to open eyelids (Teramoto, S. et al., 1988, Exp. Anim., 37:455-462). Most of these mutations show complete penetrance. However, some affect each eye variably and at least one phenotype can be reversed by a single maternal injection of steroids (Watney, M. J. & J. R. Miller, 1964, Nature 202:1029-1031). In addition, phenocopi (Juriloff, D. M. et al., 1982, Can. J. Genet. Cytol., 25:246-254). The eyelid is lined with an active zone of cell growth (Kaufman, M. H., 1992, In: The Atlas of Mouse Development. Academic Press, Harcourt Brace Jovanovich, San Diego, Calif.), and these data indicate that the effect of the anti-IFN antibodies is to block cell growth inhibition of the interferon super-sensitive trisomy 16 cells lining the eyelids.

Back Curvature. One of the most striking effects of the maternal anti-IFN treatment was the return-toward-normal of the curvature of the trisomy 16 fetus back which is frequently rounded at later stages where a concave curvature is expected. Back curvature comparisons (FIG. 2B) are restricted to fetuses from litters greater than 20 mm in length because both euploid and trisomic fetuses are expected to have rounded backs prior to the 20 mm stage (Theiler, K., 1972, In: The House Mouse, Springer, Berlin, Heidelberg, N.Y.). Back curvature was assessed by a double-blind study in which three individuals scored a rounded back as a −1, a flat back as a 0 and a convex (normal) back as a+1. There was good agreement between the scores of the three individuals (correlations ranged from 0.80 to 0.92). The mean of the three evaluations was used for comparisons.

There was no significant difference in the back curvature scores of the trisomic fetuses from uninjected and non-specific IgG injected control mothers (p=0.8236 [0.3424]). The trisomic fetuses from anti-IFN treated mothers (N=10, mean=+0.66) showed a significant return-toward-normal back curvature when compared to fetuses from untreated mothers (N=9, mean=−0.18, p=0.009 [0.009]) and the comparable fetuses from non-specific IgG treated animals (N=11, mean=−0.27, p=0.008 [0.003]).

One hundred fifty fetuses whose eyes, back, and length, appeared normal were also karyotyped (75 control and 75 anti-IFN treated). A 24 mm fetus was one of two fetuses discovered to be trisomy in this screen. A second fetus (10 mm CRL) was also found in a litter from an anti-IFN treated mother and was essentially indistinguishable from its euploid littermates. LEGEND, Table 1: Compilation of data on karyotyped trisomy 16 fetuses.

(A) Mean length of normal littermates (mm, CRL); (B) Length of trisomic fetus (mm, CRL); (C) Change in trisomic fetus length relative to its normal littermates (%); (D) Average weight of normal littermates (gm); (E) Weight of trisomy fetus (gms); (F) Opening of the eyes (mm); (G) Average back curvature scores of three individuals, +1=normal concave, 0=flat, −1=rounded.

7. EXAMPLE CONSTRUCTION OF A RECOMBINANT INTERFERON ANTAGONIST COMPRISING HUMAN INTERFERON α/β and γ RECEPTOR DOMAINS A gene encoding a fusion protein is constructed using a Glutamine-S-transferase containing expression plasmid pAcGHLT-B (PharMingen, San Diego, Calif., USA). The interferon binding domain of the human α/β interferon receptor is obtained by Nco I endonuclease digestion of plasmid p23, available from deposit No. ATCC 65007, and isolation of the 1177 bp fragment. This fragment is inserted into the Nco I site of pAcGHLT-B to yield pAcGST-23. The interferon binding domain of the human γ interferon receptor is obtained by Dsa I and Nsp I endonuclease digestion of the plasmid pUCLGRIF16, available from deposit No. ATCC 59873, and isolation of the 603 bp fragment. A Pst I-Sma I digest of pAcGST-23 is used to remove a portion of the multiple cloning site located 3' of the gene encoding the α/β interferon receptor domain and the Dsa I/Nsp I fragment of pUCLGRIF16 is inserted to yield pAcGST-23-γr. The translation product of the resultant construct, GST-α/β-γ, contains the following domains: GST-thrombin protease site-15 amino acid leader-α/β interferon receptor domain-6 amino acid spacer-γ interferon receptor domain.

A recombinant baculovirus is constructed containing the pAcGST-23-γr operably linked to the polyhedrin promoter, suitable host cells are infected and the resultant fusion protein isolated by an anti-GST affinity absorption techniques well known in the field. See, e.g., U.S. Pat. No. 4,745,071 and U.S. Pat. No. 4,879,236 to Smith et al. The isolated fusion protein is hydrolyzed with thrombin to yield the recombinant α/β-γ receptor.

TABLE 3

| Un-injected | Ln LM (mm)[N] | (A) Ln Tri (mm)[N] | (B) % ↓ (mean ± sem) | (C) Wt NLM (gm)[N] | (D) Wt Tri (gm)[N] | (E) eyes (mm) ± sem [N] | (F) Back curv. (euploid = +1) | (G) |
|---|---|---|---|---|---|---|---|---|
| 17-20 mm | 18.32[5] | 17.29[8] | −4.12 ± 1.7 | 0.60[5] | 0.486[8] | 0.490 ± 0.03[8] | −0.207 | 62 fetuses (17 trisomic) 5 resorption sites, |
| 20-23 mm | 21.26[5] | 16.83[3] | −20.67 ± 5.5 | 0.84[3] | 0.591[3] | 0.237 ± 0.12[3] | +0.333 | 13 litters |
| >23 mm | 24.63[5] | 18.40[6] | −25.50 ± 4.3 | 1.21[5] | 0.749[6] | 0.200 ± 0.06[6] | −0.443 | (mean litter size: 4.8) |
| ns-IgG | | | | | | | | |
| 17-20 mm | 18.30[4] | 16.20[5] | −11.20 ± 4.0 | 0.614[4] | 9.463[5] | 0.530 ± 0.03[5] | −0.266 | 60 fetuses (16 trisomic) 2 resorption sites, |
| 20-23 mm | 20.96[4] | 18.30[6] | −12.60 ± 2.2 | 0.796[4] | 0.526[6] | 0.283 ± 0.04[6] | −0.220 | 13 litters |
| >23 mm | 25.90[5] | 19.80[5] | −22.60 ± 9.2 | 1.460[5] | 0.911[5] | 0.127 ± 0.04[5] | −0.334 | (mean litter size: 4.6) |
| Anti-IFN | | | | | | | | |
| 17-20 mm | 18.92[5] | 18.66[8] | −2.80 ± 2.4 | 0.50[5] | 0.657[8] | 0.230 ± 0.06[8] | −0.165 | 70 fetuses (18 trisomic) 4 resorption sites, |
| 20-23 mm | 20.57[4] | 19.14[5] | −7.10 ± 3.2 | 0.78[4] | 0.643[5] | 0.176 ± 0.06[5] | ±0.530 | 13 litters |
| >23 mm | 24.59[4] | 22.38[5] | −8.40 ± 1.7 | 1.24[4] | 1.060[5] | 0.035 ± 0.03[5] | ±0.800 | (mean litter size: 5.4) |

8. CLONING OF VACCINIA IFN ANTAGONIST GENES

Viral DNA is extracted directly from live Vaccinia virus (ATCC Cat. No. VR-1354, WR Strain) using a QIAamp-DNA Mini Kit (Qiagen, Hilden, Germany, Cat. No. 51304). The DNA is then used as template for PCR amplification of the complete or truncated genes. The primers, based on the published gene sequences (B8R, GenBank Accession #AF0162273; B18R, GenBank Accession #D90076) are:

| | | |
|---|---|---|
| B8R P1: | ATGAGATATATTATAATTC | (SEQ ID NO: 5) |
| B8R P2: | TCATTAGTTAAATTTTCTCTTG | (SEQ ID NO: 6) |
| B18R P1: | AGTTACGCCATAGACATCGAA | (SEQ ID NO: 7) |
| B18R P2: | TCATTACTCCAATACTACTGTAGT | (SEQ ID NO: 8) |

After 35 PCR cycles (94.5° C. for 1 minute, 54.5° C. for 1 minute, 71.5° C. for 1.5 minutes) the incubation at 71.5° C. can be extended to 15 minutes to improve A overhang synthesis. The PCR product for the B 18R gene is shown in FIG. 4. The PCR product can then be directly cloned into a mammalian expression plasmid (e.g., pcDNA4/HisMax-TOPO (In Vitrogen, Diego, Calif., USA)). Candidate plasmids can be screened by restriction endonuclease digestion. FIG. 4 shows the digestion profile of a plasmid isolate containing the B18R gene. Confirmation of the direction of the insert is accomplished by gene amplification using one primer for a site on the plasmid and an appropriate second primer chosen from those used for the original PCR amplification. The plasmids carrying the gene in the proper orientation are extracted from transformed 250 cc *E. coli* cultures using endotoxin free conditions (for example using a Qiagen EndoFree Plasmid Maxi Kit).

The present invention is not to be limited in scope by the specific embodiments described which were intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); (Harlow, E. and Lane, D.) Using Antibodies: A Laboratory Manual (1999) Cold Spring Harbor Laboratory Press; and a series, Methods in Enzymology (Academic Press, Inc.); Short Protocols In Molecular Biology, (Ausubel et al., ed., 1995). All patents, patent applications, and publications mentioned herein, both supra and infra, are hereby incorporated by reference in their entirety.

What is claimed is:

1. A composition for reducing the incidence of pathological effects of a disease or decreasing the pathological effects of a disease, wherein the pathological effects are associated with an increased level of or a heightened responsiveness to interferon, wherein said composition consists of a combination of the isolated interferon binding proteins B18R, B8R, and a suitable pharmaceutical carrier, and wherein the composition inhibits the activity of at least two different species of interferon.

2. The composition of claim 1, wherein said at least two species of interferon comprise IFN-α and IFN-γ.

3. The composition of claim 1, wherein at least one of the interferon binding proteins is PEGylated.

4. The composition of claim 1, wherein at least one of the interferon binding proteins is fused with transferrin.

5. A method of reducing incidence of pathological effects of a disease or decreasing pathological effects of a disease, wherein said pathological effects are associated with an increased level of or heightened responsiveness to two or more interferons in a patient suffering from said disease, comprising the step of administering a therapeutically effective amount of the composition of claim 1 to said patient, wherein said therapeutically effective amount of said composition is effective to reduce incidence or decrease said pathological effects associated with an increased level of two or more interferons.

6. A method according to claim 5, wherein said disease is Alzheimer's disease.

7. The method according to claim 5, wherein said disease is Down syndrome.

8. The method according to claim 5, wherein said disease is infant encephalitis.

9. The method according to claim 5, wherein said disease is an autoimmune disease.

10. The method according to claim 5, wherein said disease is AIDS.

* * * * *